United States Patent
Ulm, III et al.

(10) Patent No.: US 12,201,312 B2
(45) Date of Patent: Jan. 21, 2025

(54) SELF-ADJUSTING CATHETER

(71) Applicant: LEGACY VENTURES LLC, Nashville, TN (US)

(72) Inventors: Arthur John Ulm, III, Nashville, TN (US); Gustavo Prado, San Diego, CA (US); Russel Corvese, Lake Forest, CA (US)

(73) Assignee: Legacy Ventures LLC, Plano, TX (US)

( * ) Notice: Subject to any disclaimer, the term of this patent is extended or adjusted under 35 U.S.C. 154(b) by 0 days.

(21) Appl. No.: 18/668,339

(22) Filed: May 20, 2024

(65) Prior Publication Data
US 2024/0307077 A1    Sep. 19, 2024

Related U.S. Application Data

(60) Provisional application No. 63/467,642, filed on May 19, 2023.

(51) Int. Cl.
*A61B 17/22* (2006.01)
*A61B 17/00* (2006.01)
*A61B 90/00* (2016.01)

(52) U.S. Cl.
CPC ........ *A61B 17/22* (2013.01); *A61B 17/00234* (2013.01); *A61B 90/39* (2016.02);
(Continued)

(58) Field of Classification Search
CPC ........... A61B 2017/22051; A61B 2017/22052; A61B 2017/22054; A61B 2017/22055;
(Continued)

(56) References Cited

U.S. PATENT DOCUMENTS 4,531,943 A * 7/1985 Van Tassel ............ A61N 1/056
                                                604/523
5,358,493 A   10/1994 Schweich, Jr. et al.
(Continued)

FOREIGN PATENT DOCUMENTS

WO    2022146946 A1    7/2022

OTHER PUBLICATIONS

Emi Kuriyama et al., Analysis of the Anatomical Factors Affecting Ability to Navigate Penumbra Catheter through Internal Carotid Siphon, Jour. Neuroendovascular Therapy 2020, vol. 14, No. 5, pp. 169-176, Department of Neurosurgery, Wakayama Medical University, Wakayama, Japan.
(Continued)

*Primary Examiner* — Thomas McEvoy
(74) *Attorney, Agent, or Firm* — Shane Cortesi

(57) ABSTRACT

Catheters and uses of same are described. The catheter may be an aspiration or distal access catheter used to treat stroke or other neurovascular conditions and may include a proximal segment and a distal segment with fixed shapes and outer diameters, and a distensible segment that is located proximal to the distal segment and adjacent to the catheter distal end and that is configured to undergo a conformation change when the catheter open distal end is lodged against the wall of a human blood vessel and a surgeon is attempting to move the catheter distally through the human blood vessel. The catheter may include a wall that is comprised of an inner tube surrounding the catheter's hollow interior, a coil surrounding the inner tube, a braid surrounding the coil and/or an outer tube surrounding the braid. The pitch of the coil may be greater in the distensible segment as compared to the proximal segment and the outer tube may not be attached to the inner tube for at least a portion of the distensible segment, which features allow for the distensible
(Continued)

segment to undergo the conformational change. The distal segment may include a metallic marker band, providing rigidity to the distal segment.

30 Claims, 22 Drawing Sheets

(52) U.S. Cl.
CPC .............. *A61B 2017/00238* (2013.01); *A61B 2017/00292* (2013.01); *A61B 2017/00544* (2013.01); *A61B 2017/00561* (2013.01); *A61B 2017/0084* (2013.01); *A61B 2017/00862* (2013.01); *A61B 2017/00942* (2013.01); *A61B 2017/22079* (2013.01); *A61B 2090/3966* (2016.02); *A61B 2217/005* (2013.01)

(58) Field of Classification Search
CPC ........... A61B 2017/22061; A61B 2017/22062; A61B 2017/22064; A61B 2017/22065; A61B 2017/22067; A61B 2017/22068; A61B 2017/22069; A61B 2017/22079; A61M 25/0074; A61M 2025/0081; A61M 25/008; A61M 2025/1097; A61M 2025/1095; A61M 2025/1093; A61M 2025/109; A61M 2025/1088; A61M 2025/1086; A61M 2025/1084; A61M 2025/1081; A61M 2025/1079; A61M 2025/1077; A61M 2025/1075; A61M 2025/1072; A61M 2025/107; A61M 2025/1068; A61M 2025/1065; A61M 2025/1063; A61M 2025/1061; A61M 2025/1059; A61M 2025/1056; A61M 2025/1054; A61M 2025/1052; A61M 2025/105; A61M 2025/1047; A61M 2025/1045; A61M 2025/1043; A61M 25/104; A61M 2025/1015; A61M 2025/1013; A61M 25/1011; A61M 25/1006; A61M 2025/1004; A61M 25/1002; A61M 25/10
See application file for complete search history.

(56) References Cited

U.S. PATENT DOCUMENTS

| | | |
|---|---|---|
| 5,599,319 A | 2/1997 | Stevens |
| 6,059,769 A | 5/2000 | Lunn et al. |
| 7,766,896 B2 | 8/2010 | Kornkven Volk et al. |
| 8,366,735 B2 | 2/2013 | Bose et al. |
| 10,058,235 B2 | 8/2018 | Gunday et al. |
| 10,245,413 B2 | 4/2019 | Shimada et al. |
| 11,400,255 B1 | 8/2022 | Chou et al. |
| 11,534,575 B2 | 12/2022 | Garrison et al. |
| 2005/0187536 A1* | 8/2005 | Shelso .............. A61M 25/0069 604/528 |
| 2007/0213687 A1 | 9/2007 | Barlow |
| 2010/0137892 A1* | 6/2010 | Krolik ............ A61B 17/320725 606/159 |
| 2016/0310148 A1* | 10/2016 | Allen ................ A61B 17/12136 |
| 2017/0105743 A1* | 4/2017 | Vale .................. A61B 17/22032 |
| 2021/0386429 A1* | 12/2021 | Franano ........... A61B 17/12113 |
| 2024/0350288 A1* | 10/2024 | Ueda ................... A61M 25/104 |

OTHER PUBLICATIONS

International Search Report in corresponding International Application No. PCT/US2024/030169, 4 pp.

* cited by examiner

SELF-ADJUSTING CATHETER

BACKGROUND

Technical Field

The present application relates to catheters.

Background of the Invention

Aspiration catheters (also known as suction catheters) enter the body through the groin and are used to go up to the brain to suck a clot out of a blood vessel of an ischemic stroke patient using a syringe or other suction force attached to the suction catheter proximal end. Typical suction catheters are made of braided material, nitinol (memory metal), nylon etc. and are designed to resist deformation widthwise along their entire length. Examples of suction catheters in use in thrombectomy procedures (removal of clots from blood vessels) include, for example, the PENUMBRA SYSTEM (Penumbra Inc., Alameda, California) and the catheters described in Penumbra Inc.'s U.S. Pat. No. 8,366,735, the contents of which are incorporated herein by reference.

Unfortunately, the vessels going to the brain are tortuous and catheters often get stuck at the turns of either the cavernous sinus or petrous bone. In particular, as shown in FIGS. 1-4, when pushing the catheter 10' distally, the catheter distal end 12' (the furthest from the surgeon) gets stuck on the vessel wall 14'. More specifically, in thrombectomy procedures, often the catheter distal end 12' gets stuck on the ledge 16' where the ophthalmic artery 18' branches away from the internal carotid artery 20', and when the surgeon pushes on the catheter's proximal end to try to dislodge the catheter distal end 12' from the ledge 16', a proximal segment 24' of the catheter 10' kinks and folds back onto itself, due to the fact that the surgeon is pushing the proximal end 22' distally and the ledge 16' is pushing back on the catheter 10' in the proximal direction. As a result, the surgeon cannot access the clot 104'. The ledge effect of the PENUMBRA SYSTEM is described in, for example, Kuriyama et al., Analysis of the Anatomical Factors Affecting Ability to Navigate Penumbra Catheter Through Internal Carotid Siphon, Journal of Neuroendovascular Therapy 2020; 14: 169-176.

One approach to the problem has been the use of guide wires. However, using a guide wire can be problematic because they can disrupt the clot, and moreover, guide wires add to the time of the procedure, which is problematic, because time is critical when treating stroke.

U.S. Pat. No. 5,358,493 describes an access catheter that has a proximally relatively stiff section, a distal section that is more flexible than the proximal section and an intermediate section between the proximal and distal sections that provides a transition to flexibility between the proximal and distal ends. It is unclear whether the '493 patent was ever commercialized. Nonetheless, there is a need for suction and other catheters that that are better able to navigate branch points, such as the turns of the cavernous sinus and petrous bone.

BRIEF DESCRIPTION OF THE DRAWINGS

as shown in FIG. 3, the prior art catheter is attempting to reach a clot in a distal vessel.

in FIG. 5, the catheter is in a relaxed configuration (is not being pushed into the vessel wall) and has a uniform width.

in FIG. 6, the catheter is in a relaxed configuration (is not being pushed into the vessel wall) and has a uniform width.

as shown in FIG. 8, the catheter is attempting to reach a clot in a distal vessel and is in a relaxed configuration.

as shown in FIG. 14, the coil pitch is greater in the distensible segment.

SUMMARY OF INVENTION

Figure 1:
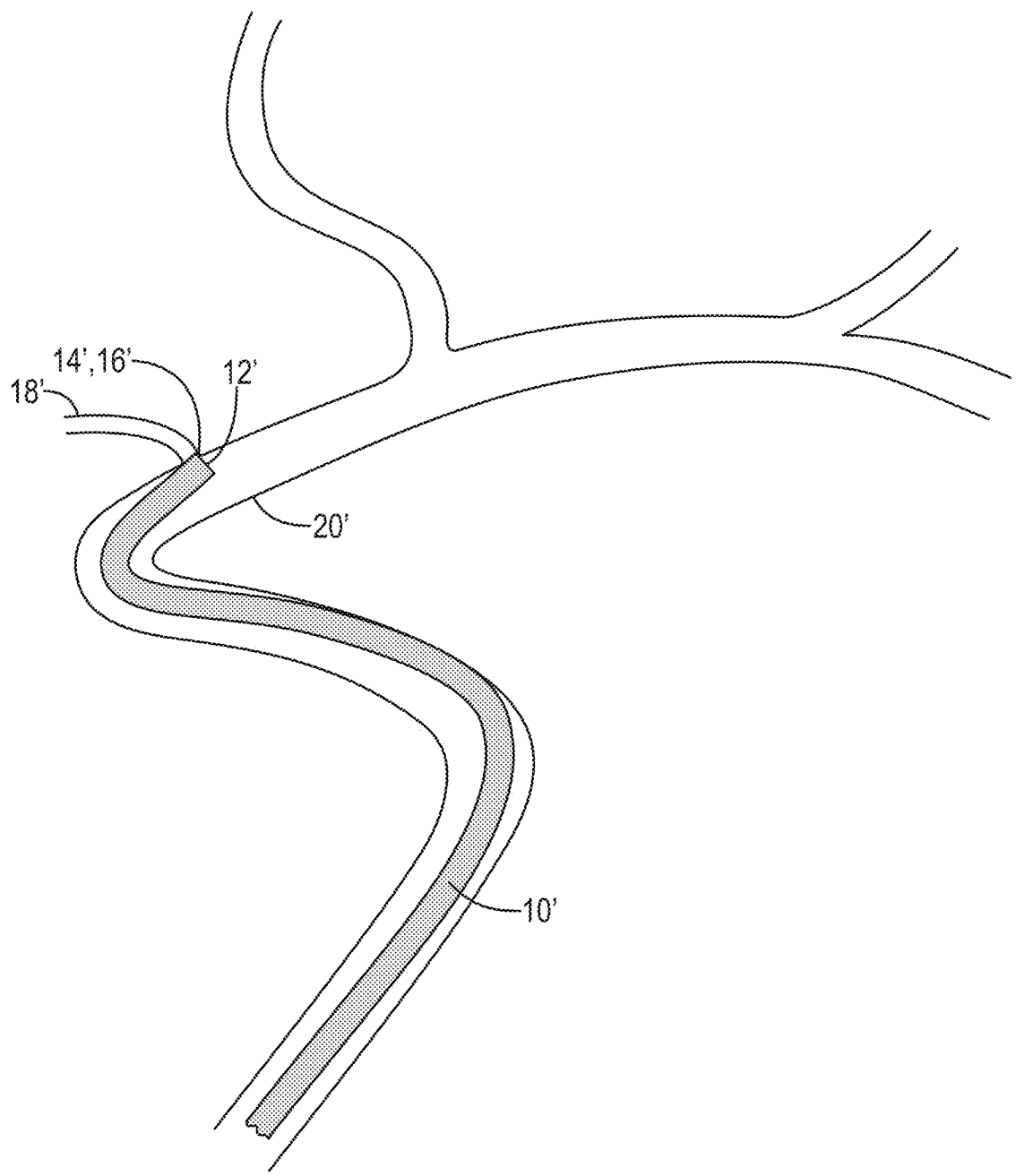
FIG. 1. illustrates a prior art catheter in a vessel with the distal end of the prior art catheter lodged against the vessel wall.
Figure 2:
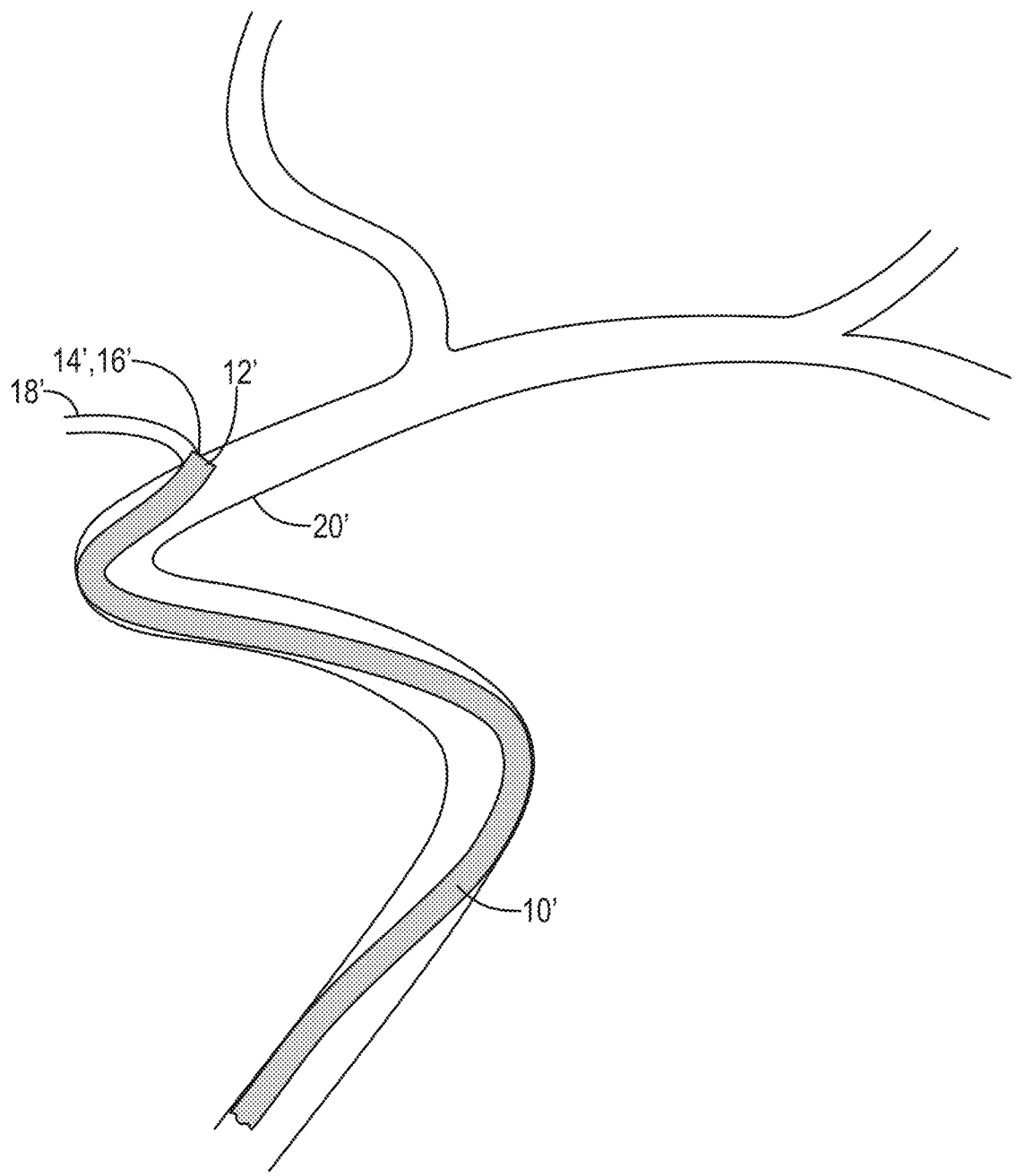
FIG. 2 illustrates the configuration of the prior art catheter of FIG. 1 when the surgeon continues to move the prior art catheter proximal end in the distal direction.
Figure 3:
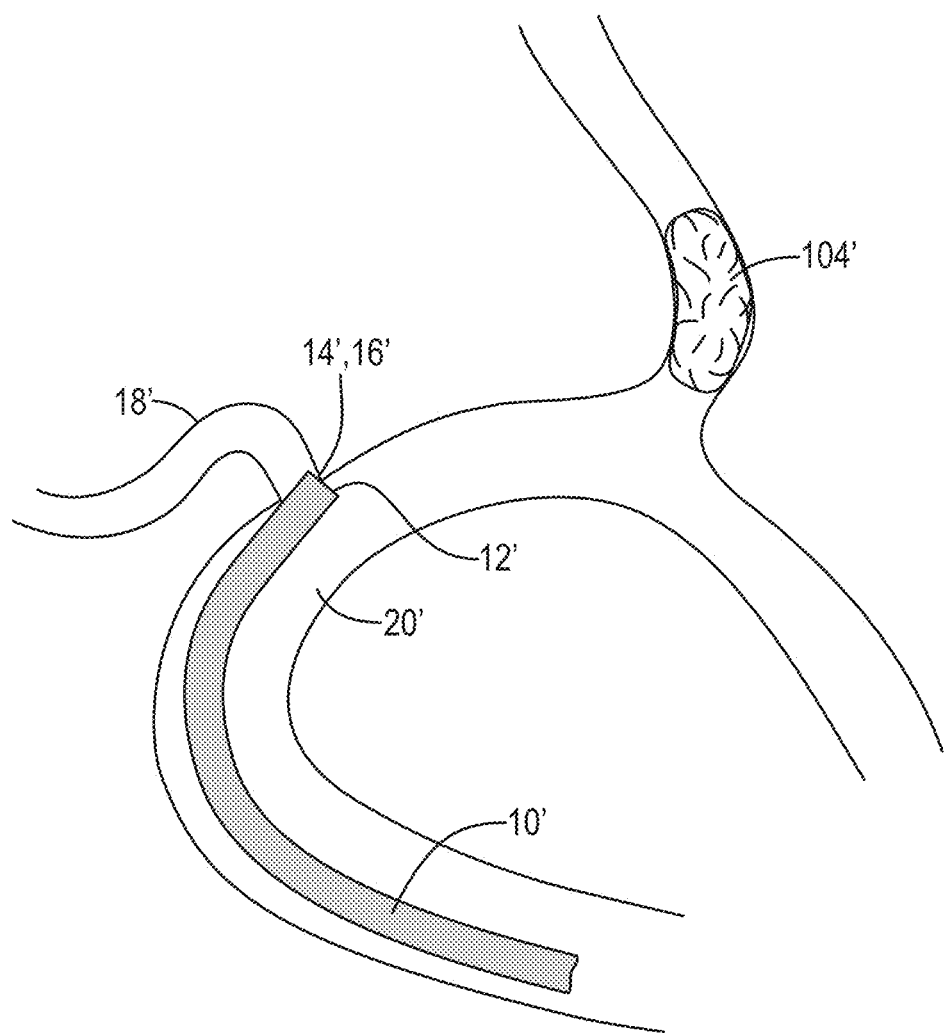
FIG. 3. also illustrates a prior art catheter in a vessel with the distal end of the prior art catheter lodged against the vessel wall.

In some embodiments, the present disclosure provides a catheter that may include a catheter proximal end (which may be open); a catheter open distal end; a length extending from the catheter proximal end to the catheter open distal end; a height perpendicular to the length; a width perpendicular to the length and height; a hollow interior/lumen extending from the catheter proximal end to the catheter open distal end; a proximal segment that may comprise a proximal segment proximal end, a proximal segment distal end located proximal to the catheter open distal end, a proximal segment length extending from the proximal segment proximal end to the proximal segment distal end and parallel to the catheter length, a proximal segment width parallel to the catheter width, and/or a proximal segment height parallel to the catheter height; and/or a distensible segment that may comprise a distensible segment proximal end located distal to the proximal segment distal end, a distensible segment distal end located proximal to the catheter open distal end, a distensible segment length extending from the distensible segment proximal end to the distensible segment distal end and parallel to the catheter length, a distensible segment width parallel to the catheter width, and/or a distensible segment height parallel to the catheter height; a distal segment that may comprise a distal segment proximal end located distal to the distensible segment distal end, a distal segment distal end, a distal segment length extending from the distal segment proximal end to the distal segment distal end and parallel to the catheter length, a distal segment width parallel to the catheter width, and/or a distal segment height parallel to the catheter height.

Optionally, the catheter is intended for neurovascular use (e.g., as a distal access catheter or aspiration catheter). Optionally, the length of the catheter is from about 100 centimeters to about 165 centimeters. Optionally, the catheter comprises a relaxed configuration in which the proximal, distal and distensible segments are cylindrical in shape and comprise an inner diameter of from about 0.04 inches to about 0.10 inches. Optionally, the distensible segment is configured to undergo a conformational change (and the proximal and distal segments are configured to maintain a fixed cylindrical shape and length and diameter) when a linear force in the distal direction is applied to the catheter and, in turn, a linear force in the proximal direction is applied to the catheter open distal end. For example, optionally, when a surgeon attempts to push the catheter distally in a blood vessel when the catheter open distal end is lodged against a vessel wall (i.e., when a linear force in the distal direction is applied to catheter proximal end and, in response, a linear force in the proximal direction is applied to the proximal segment), the catheter is configured to self-adjust from the relaxed configuration to a distended configuration in which i) the cross-sectional height and/or width of the distensible segment is configured to increase, the distensible segment is configured to become non-cylindrical, and/or at least one side of the catheter in the distensible segment is configured to bulge outward, and ii) the cross-sectional width, cross-sectional height and length of the proximal and distal segments are configured to remain constant and the proximal and distal segments are configured to remain cylindrical. Optionally, in the distended configuration, the proximal segment does not kink. Optionally, the catheter is configured to self-adjust from the distended configuration to the relaxed configuration when the catheter open distal end dislodges from the vessel wall (i.e., when the linear force in the proximal direction acting on the catheter open distal end is removed). Optionally, in the distended configuration, the length of the distensible segment is configured to decrease. Optionally, in the distended configuration, the distensible segment is a non-cylindrical shape (e.g., one side of the distensible segment shortens and curves inward and an opposite side lengthens and bulges outward). Optionally, the length of the distensible segment is from about 5 millimeters to about 10 millimeters. Optionally, the length of the proximal segment is at least ten times greater than the length of the distensible segment and the length of the distal segment. Optionally, the length of the distensible segment is greater than the length of the distal segment. Optionally, the distal end of the distensible segment is located about 0.5 millimeters to about 5 millimeters from the catheter open distal end (e.g., preferably about 1.5 mm). Optionally, the catheter is coupled to a suction source. Optionally, the suction source is a syringe or pump. Optionally, the distal segment comprises a cylindrical metallic band located distal to the distensible segment distal end and adjacent to the catheter open distal end. Optionally, the cylindrical metallic band is located from about 0 millimeters to about 5 millimeters distal to the distensible segment distal end. Optionally, the cylindrical metallic band is located from about 0 millimeters to about 5 millimeters proximal to the catheter open distal end. Optionally, the cylindrical metallic band comprises a length parallel to the catheter length and further wherein the length of the cylindrical metallic band is less than the length of the distensible segment. Optionally, the cylindrical metallic band is more visible under x-ray as compared to the distensible segment when the catheter is located in a cranial blood vessel inside the body of a human and the x-ray is taken from outside the human's body. Optionally, the cylindrical metallic band, the proximal segment and the distal segment have substantially the same inner diameter in the relaxed configuration and further wherein the cylindrical metallic band, the proximal segment and the distal segment have substantially the same outer diameter in the relaxed configuration. Optionally, the cylindrical metallic band is comprised of tantalum, platinum and/or iridium. Optionally, the distal segment extends from the distensible segment distal end to the catheter open distal end. Optionally, the proximal segment extends from the open proximal end to the distensible segment proximal end. Optionally, the catheter further comprises a wall extending from at least the proximal segment to the distal segment (and preferably from the catheter proximal end to the catheter open distal end), the wall comprised of an inner layer (e.g., inner tube) surrounding the hollow interior and an outer layer (e.g., outer tube) extending around the inner tube, wherein the outer tube is attached to the inner tube in the proximal and distal segments, and further wherein the outer tube is not attached to the inner tube for at least a portion of the distensible segment. Optionally, the wall of at least a portion of the proximal segment and at least a portion of the distensible segment further comprises a plurality of ribs (e.g. a coil located between the outer tube and the inner tube). Optionally, for at least a portion of the distensible segment, the coil is attached to the inner tube but not to the outer tube, and further wherein, in the proximal segment, the coil is attached to the inner tube and the outer tube. Optionally, the coil extends around the inner tube in a helical manner, the coil comprising a variable coil pitch, and further wherein the coil pitch in the distensible segment is greater than the coil pitch in the proximal segment. Optionally, the wall further comprises a braid located between the coil and the outer tube. Optionally, the distal segment comprises a cylindrical metallic band located distal to the distensible segment distal end and adjacent to the catheter open distal end, with the cylindrical metallic band attached to the braid. Optionally, the coil pitch in the distensible segment is configured to change while the coil pitch in the proximal segment remains constant when the catheter self-adjusts from the relaxed configuration to the distended configuration. Optionally, for at least a portion of the distensible segment, the braid is attached to the inner tube but not to the outer tube, and further wherein, in the proximal segment and the distal segment, the braid is attached to the inner tube and the outer tube. Optionally, the coil pitch in the distensible segment is between about 0.006 to 0.040 inches and further wherein the coil pitch in the proximal segment is between about 0.002 to about 0.006 inches. Optionally, the coil pitch in the distensible segment is between about 0.015 to 0.040 inches and further wherein the coil pitch in the proximal segment is between about 0.002 to about 0.006 inches. Optionally, the coil is metallic (e.g., steel or nitinol). Optionally, the inner tube and the outer tube are comprised of an elastomeric material. Optionally, in the relaxed configuration, the catheter comprises a substantially constant inner diameter and a substantially constant outer diameter along the catheter length. Optionally, in the relaxed configuration, the catheter comprises an inner diameter of from about 0.06 to about 0.08 inches and an outer diameter of from about 0.08 to about 0.1 inches. Optionally, the catheter comprises a plurality of distensible segments, each distensible segment separated by a proximal segment. Optionally, the catheter is comprised of a biocompatible material and is sterile. Optionally, the distensible segment is configured to bend while the proximal segment and distal segment remains constant when the catheter self-adjusts from the relaxed configuration to the distended configuration. Optionally, the inner tube and/or the outer tube comprise a plurality of tubes joined together (e.g., the materials forming the inner and outer layer may be comprised of progressively softer materials distally to provide more flexibility—i.e., the distal tubes may be more flexible than the proximal tubes). Optionally, the braid, coil, outer tube, and/or inner tube extend substantially to the full length of the catheter (e.g., at least 90% of the full length of the catheter). For example, the distal end of the coil may be located under the cylindrical metallic band.

In still further embodiments, the present disclosure provides a method of using the catheter in a human vascular system comprising providing the catheter, inserting the catheter open distal end into the human vascular system and moving the catheter open distal end distally in the human blood vessel. Optionally, a human blood vessel of the human vascular system comprises a clot, the catheter proximal end is coupled to a suction source, and the method further comprises using suction to draw the clot toward the catheter distal end to remove the clot from the human blood vessel. Optionally, the method further comprises using a stent retriever in conjunction with the catheter to remove the clot from the human blood vessel. Optionally, the method further comprises pushing the catheter distally, allowing the catheter open distal end to contact and become stuck against a wall of a human blood vessel of the vascular system, and continuing to push the catheter proximal end distally so that the catheter open distal end moves towards a center of the human blood vessel to become dislodged from the vessel wall. Optionally, prior to the catheter open distal end becoming dislodged from the vessel wall, i) the height and/or width of the distensible segment increases, the distensible segment becomes non-cylindrical, and/or at least one side of the catheter bulges outward, and ii) the width, height and length of the proximal and distal segments stay constant and the proximal and distal segments remain cylindrical. Optionally, prior to the catheter open distal end moving towards the center of the human blood vessel to become dislodged from the vessel wall, the distensible segment moves away from the vessel wall then towards the vessel wall to cause the catheter open distal end to move towards the center of the vessel to become dislodged from the vessel wall. Optionally, the human blood vessel is the internal carotid artery. Optionally, the method further comprises moving a microcatheter or other neurovascular device distally through the hollow interior (e.g., to access a vessel distal to the ophthalmic artery).

In still further embodiments, the catheter is used in a method that comprises inserting the catheter open distal end into the human vascular system, passing the catheter distal end beyond the turns of the cavernous sinus and petrous bone. Optionally, the method further comprises applying suction to draw a clot or other object toward the catheter open distal end. Optionally, the method further comprises deploying a microcatheter or other neurovascular device from the open distal end.

In still further embodiments, the present disclosure provides a catheter that may include a catheter proximal end (which may be open); a catheter open distal end; a length extending from the catheter proximal end to the catheter open distal end; a height perpendicular to the length; a width perpendicular to the length and height; a hollow interior/ lumen extending from the catheter proximal end to the catheter open distal end; a proximal segment that may comprise a proximal segment proximal end, a proximal segment distal end located proximal to the catheter open distal end, a proximal segment length extending from the proximal segment proximal end to the proximal segment distal end and parallel to the catheter length, a proximal segment width parallel to the catheter width, and/or a proximal segment height parallel to the catheter height; a distensible segment that may comprise a distensible segment proximal end located distal to the proximal segment distal end, a distensible segment distal end located proximal to the catheter open distal end, a distensible segment length extending from the distensible segment proximal end to the distensible segment distal end and parallel to the catheter length, a distensible segment width parallel to the catheter width, and/or a distensible segment height parallel to the catheter height; a distal segment that may comprise a distal segment proximal end located distal to the distensible segment distal end, a distal segment distal end, a distal segment length extending from the distal segment proximal end to the distal segment distal end and parallel to the catheter length, a distal segment width parallel to the catheter width, and/or a distal segment height parallel to the catheter height; and/or a wall that may be comprised of an inner tube, a coil and/or an outer tube. Optionally, the catheter includes one or more features described above, including, for example, the aforementioned metallic band, braid, coil pitch, and selective attachment of the outer tube to the inner tube, coil and braid. Optionally, the catheter is used in one or more of the methods described above.

In still further embodiments, the present disclosure provides a catheter that may include a catheter proximal end (which may be open); a catheter open distal end; a length extending from the catheter proximal end to the catheter open distal end; a height perpendicular to the length; a width perpendicular to the length and height; a hollow interior/lumen extending from the catheter proximal end to the catheter open distal end; a proximal segment that may comprise a proximal segment proximal end, a proximal segment distal end located proximal to the catheter open distal end, a proximal segment length extending from the proximal segment proximal end to the proximal segment distal end and parallel to the catheter length, a proximal segment width parallel to the catheter width, and/or a proximal segment height parallel to the catheter height; a distensible segment that may comprise a distensible segment proximal end located distal to the proximal segment distal end, a distensible segment distal end located proximal to the catheter open distal end, a distensible segment length extending from the distensible segment proximal end to the distensible segment distal end and parallel to the catheter length, a distensible segment width parallel to the catheter width, and/or a distensible segment height parallel to the catheter height; and/or distal segment that may comprise a distal segment proximal end located distal to the distensible segment distal end, a distal segment distal end, a distal segment length extending from the distal segment proximal end to the distal segment distal end and parallel to the catheter length, a distal segment width parallel to the catheter width, and/or a distal segment height parallel to the catheter height; and the catheter comprises one or more of the following features (alone or in any combination): i) wherein the distensible segment is more flexible than the proximal segment and the distal segment; ii) wherein at least a portion of a wall of the proximal segment and at least a portion of the distensible segment comprise a plurality of ribs (e.g., coils) spaced apart and further wherein the spacing between at least some of the adjacent ribs is greater in the distensible segment than in the proximal segment; iii) wherein a wall of at least a portion of the proximal segment and/or distal segment comprises an outer layer (e.g., outer tube) that is attached to an inner layer (e.g., inner tube) and a wall of at least a portion of the distensible segment comprises an outer layer (e.g., outer tube) that is not attached to an inner layer (e.g., inner tube); iv) wherein the distensible segment and proximal segment comprise a plurality of ribs (e.g., coils forming a portion of the wall of the catheter) spaced apart and further wherein the spacing between at least some of the adjacent ribs in the distensible segment but not in the proximal segment is configured to increase when the catheter open distal end becomes lodged against a wall of a blood vessel and the catheter is pushed proximally; v) wherein the distal segment comprises a metallic band; and/or vi) wherein the distensible segment has a variable height, width, length and/or shape and the proximal segment and the distal segment have a fixed height, width, length and/or shape. Optionally, the catheter includes one or more features described above. Optionally, the catheter is used in one or more of the methods described above.

DETAILED DESCRIPTION

Figure 17:
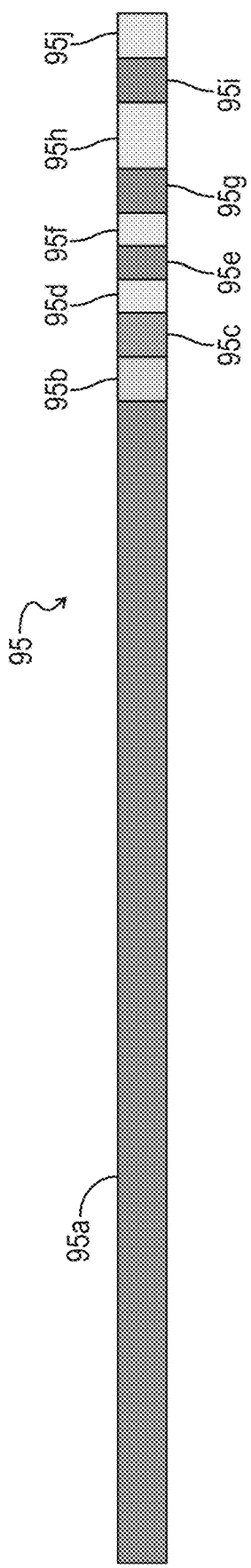
FIG. 17 illustrates an outer tube of a catheter of one embodiment of the present invention, showing how the outer tube may be made of multiple segments that increase in softness and flexibility in the distal direction.
Figure 18:
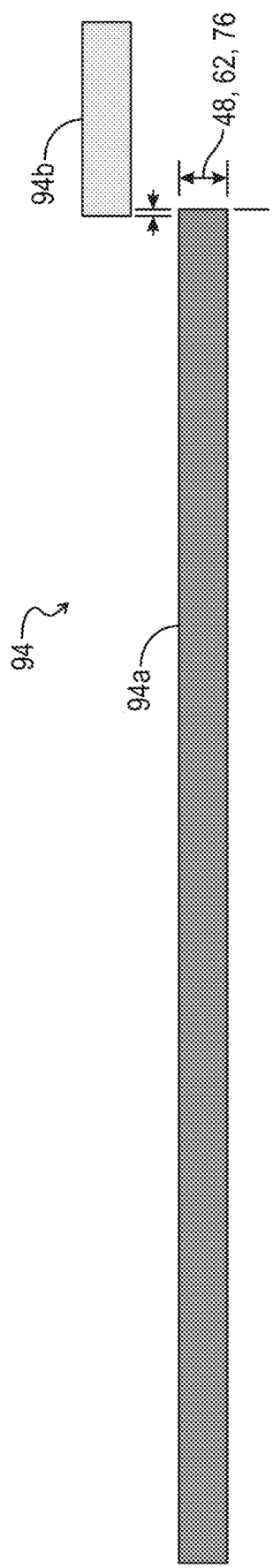
FIG. 18 illustrates an outer tube of a catheter of one embodiment of the present invention, showing how the outer tube may be made of multiple segments that increase in softness and flexibility in the distal direction.
Figure 19:
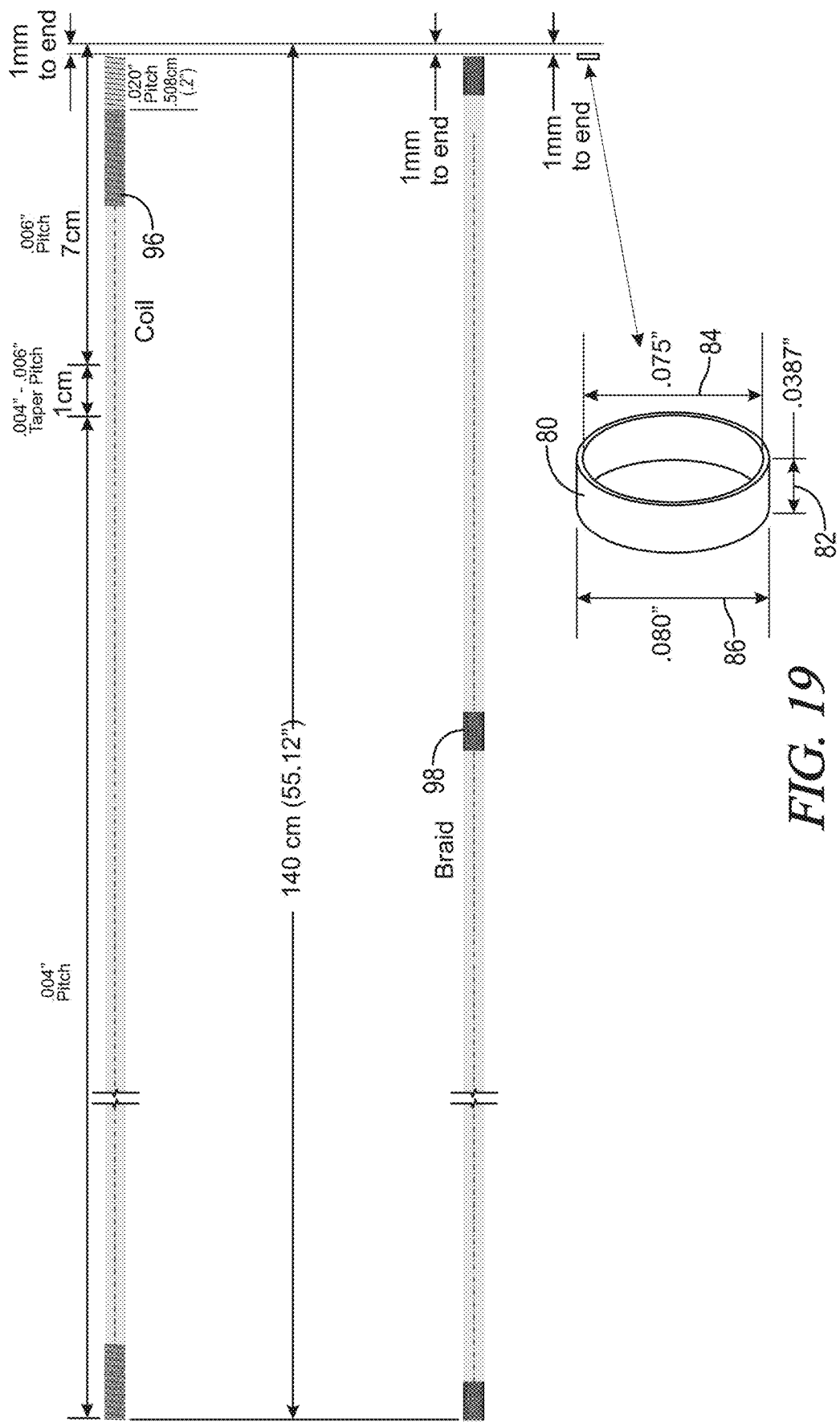
FIG. 19 illustrates a schematic view of a coil, a braid, and a band of a catheter in accordance with one embodiment of the present invention.

Referring to FIGS. 5-28, in some embodiments, the present disclosure provides a catheter, generally designated by the numeral 10. FIGS. 12-16 are drawn to scale, FIGS. 17-19 are drawn to scale lengthwise, FIGS. 4-11 and 20-28 are not drawn to scale. It will be appreciated that the proportional dimensions provided in FIGS. 12-19 are exemplary and that other dimensions are possible.

Figure 11:
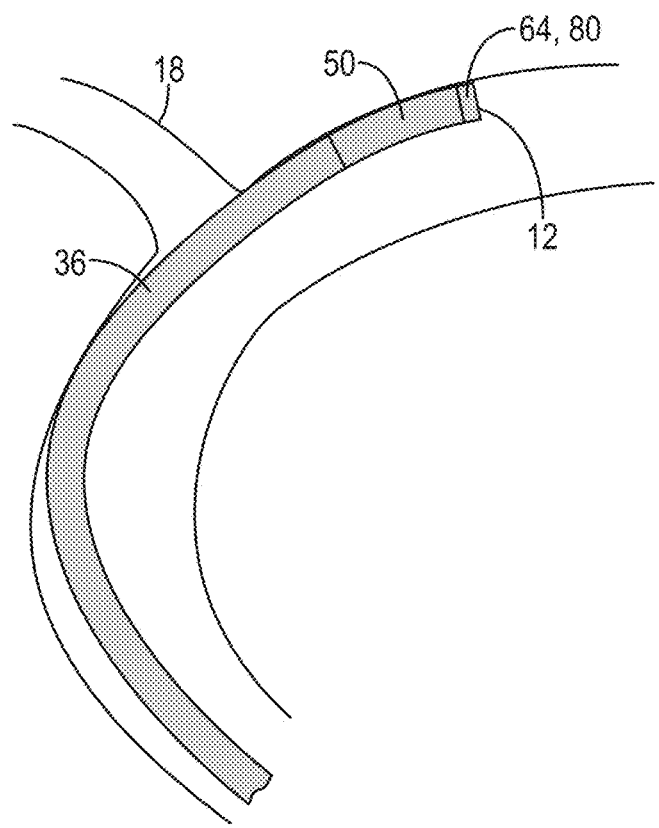
FIG. 11 illustrates the catheters of FIGS. 10 and 10A after the catheter dislodges itself from the vessel wall and returns to its relaxed configuration.
Figure 11A:
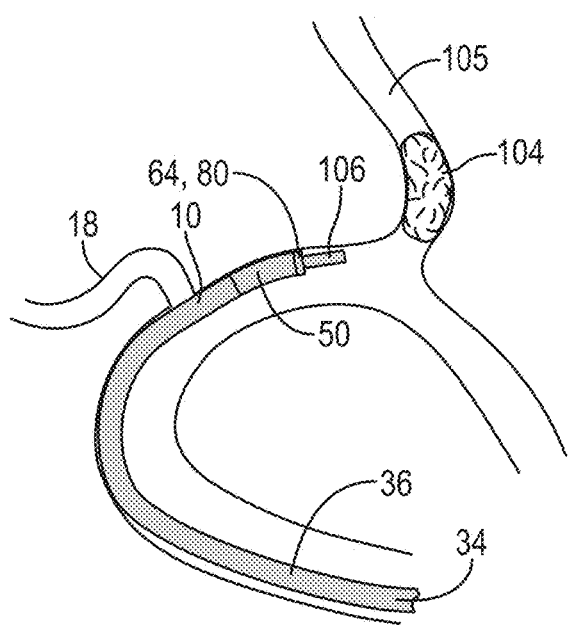
FIG. 11A illustrates how a catheter in accordance with one embodiment of the present invention may be used as a distal access catheter to deliver a microcatheter.
Figure 11B:
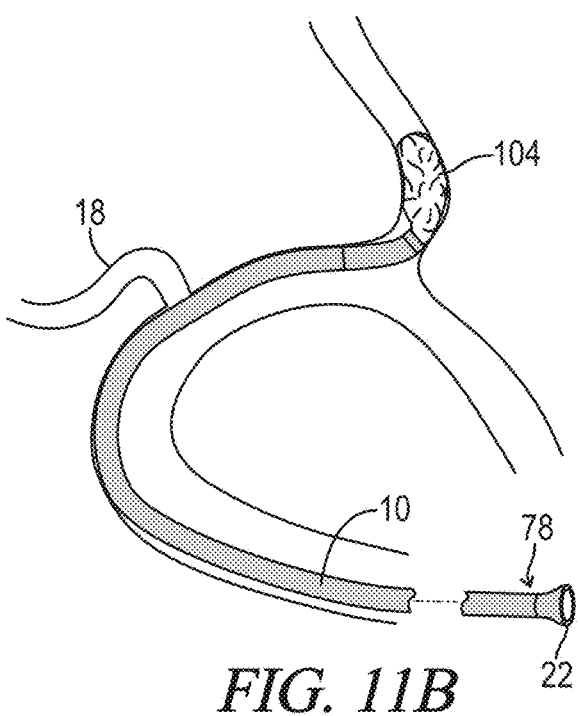
FIG. 11B illustrates how a catheter in accordance with one embodiment of the present invention may be used as an aspiration catheter to remove a clot.

The catheters of the present disclosure 10 are preferably specifically designed to avoid the aforementioned ledge 16 effect and access a human blood vessel 105 distal to the ophthalmic artery 18, as shown in FIGS. 11A and 11B for example. For example, in some embodiments, the catheter 10 may be used as an aspiration catheter or a distal access catheter. More particularly, in some embodiments, as shown in FIG. 11A, if the catheter 10 is used as a distal access catheter, a microcatheter 106 or other neurovascular device may be moved through the lumen/hollow interior 34 of the catheter 10 to, for example, access a human blood vessel 105 distal to the ophthalmic artery 18. If the catheter 10 is used as an aspiration catheter, as shown in FIG. 11B, the catheter proximal end 22 may be configured to couple to a suction source, such as a pump or syringe (not shown), via a tapered hub 78, for example, and the suction source may be configured to draw a clot 104 or other object located distal to the catheter's distal end 64 toward the catheter distal end 12 (and optionally into the catheter distal end 12 and proximally within the catheter interior towards the suction source).

With reference to FIGS. 5-28, in some embodiments, the present disclosure provides a catheter 10 that, like a typical catheter, may include an interior/lumen 34 (which may be hollow), a catheter proximal end 22 that may be open and lead to the interior 34, a catheter distal end 12 that may be open and lead to the interior 34, a length extending from the catheter proximal end 22 to the catheter distal end 12, and a width 32 perpendicular to the length 28 and a height 30 perpendicular to the width 32 and length 28.

Figure 4:
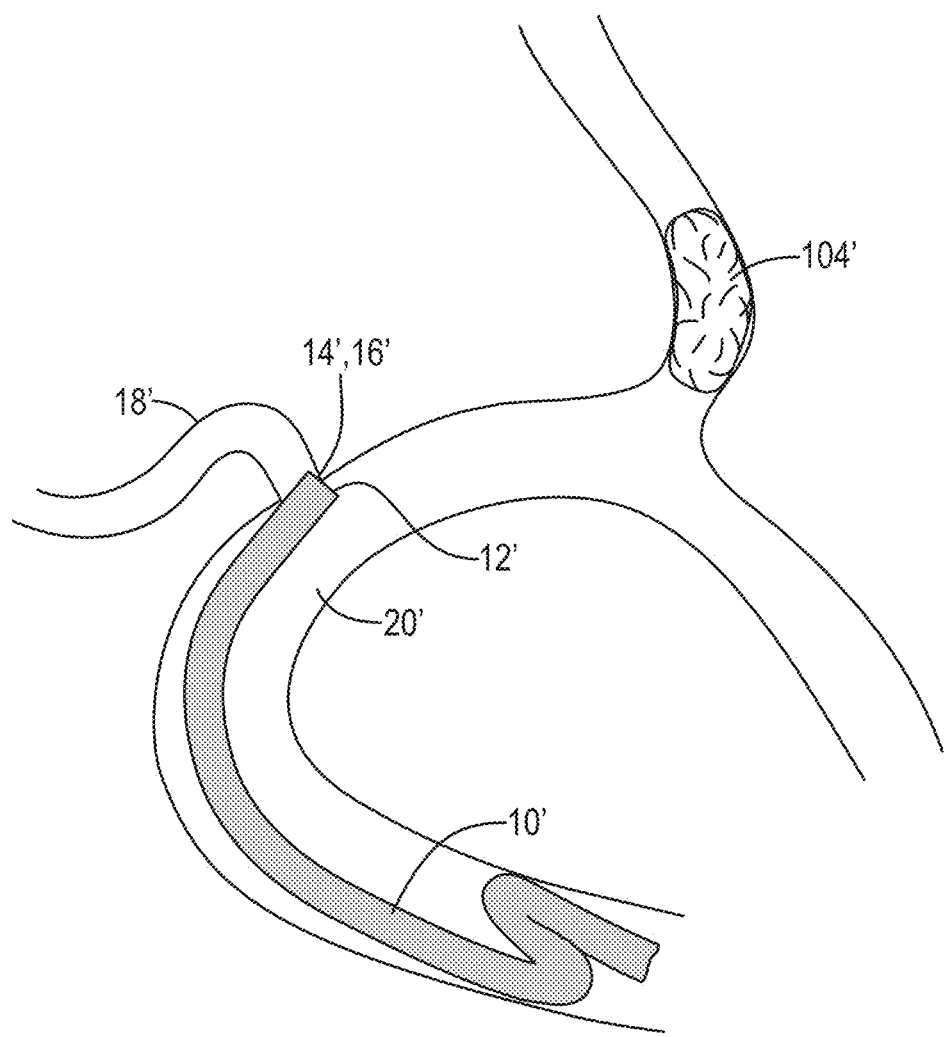
FIG. 4 illustrates the configuration of the prior art catheter of FIG. 3 when the surgeon continues to move the prior art catheter proximal end in the distal direction—i.e., a proximal portion kinks.
Figure 5:
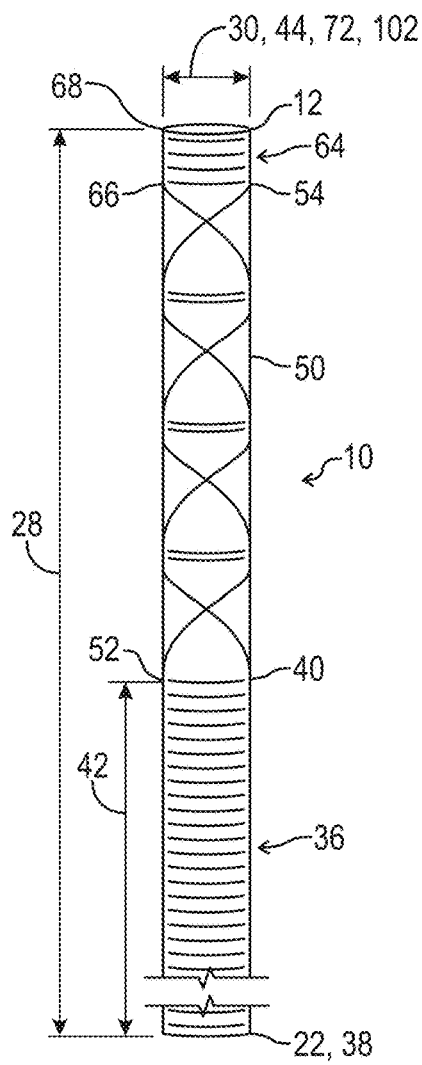
FIG. 5 illustrates a side perspective view of a distal portion of a catheter in accordance with one embodiment of the present invention.
Figure 6:
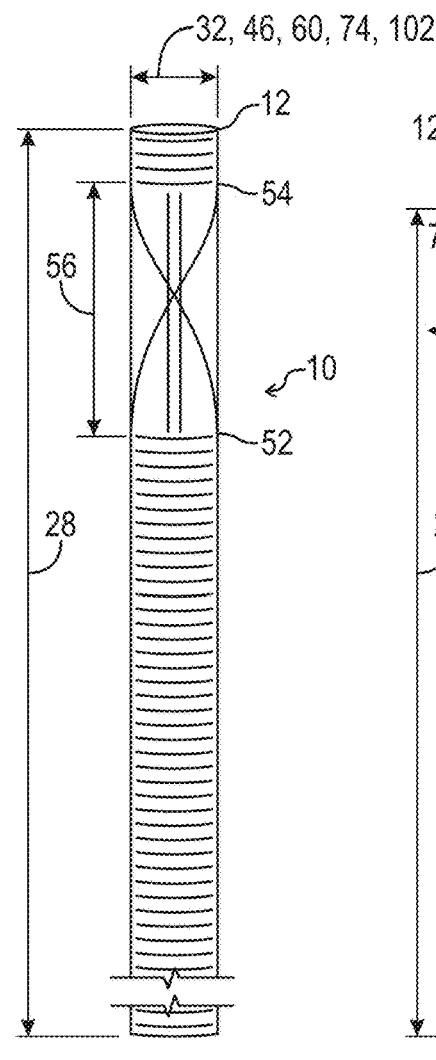
FIG. 6 illustrates a side perspective view of a distal portion of a catheter in accordance with another embodiment of the present invention.
Figure 7:
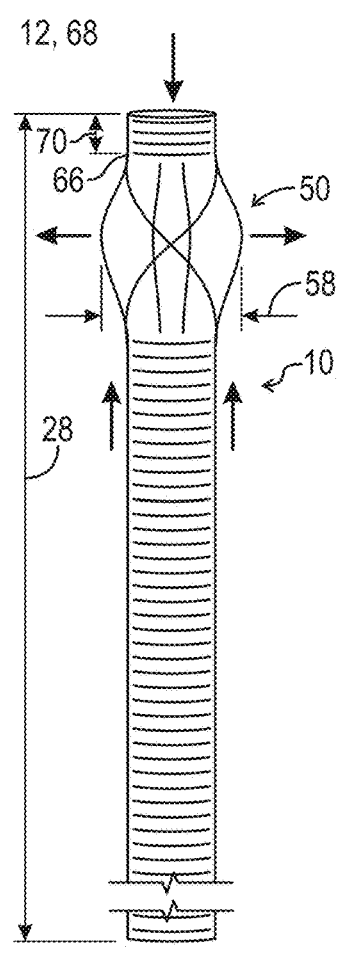
FIG. 7 illustrates a side perspective view of the distal portion of the catheter of FIG. 5 with the up and down arrows showing the proximal and distal linear force exerted on the catheter and the side arrows showing how the catheter is responding to that force by bulging outward—i.e., transitioning to a distended configuration.
Figure 9:
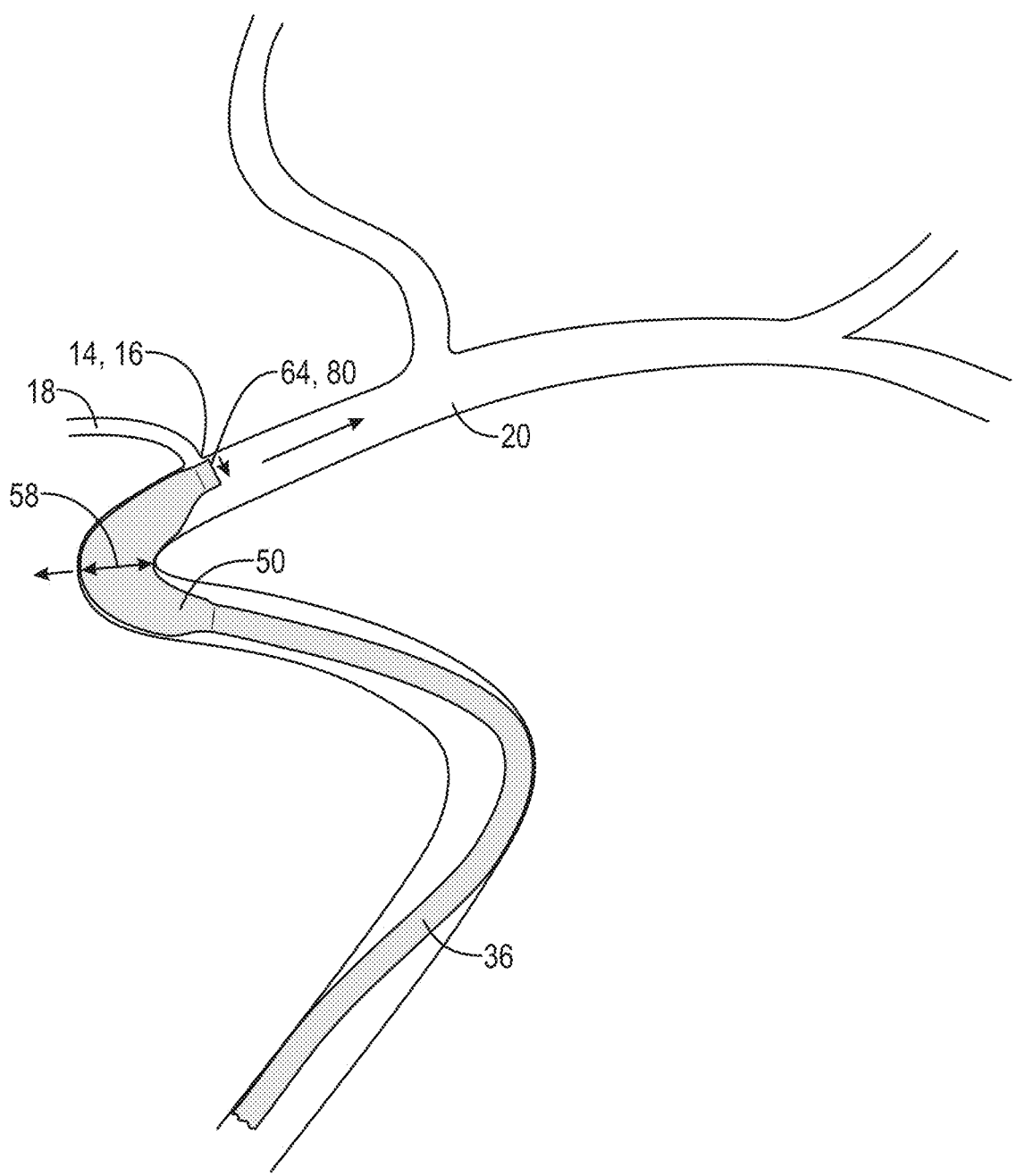
FIG. 9 illustrates how a catheter in accordance with one embodiment of the present invention may self adjust to a distended configuration to dislodge itself from the vessel wall when the surgeon continues to move the catheter proximal end in the distal direction.

Unlike typical catheters, in some embodiments, the catheter 10 is comprised of at least one segment, i.e., a distensible segment 50, that is located between a proximal segment 36 and a distal segment 64, that is designed differently from the proximal segment 36 and the distal segment 64, and is designed to behave differently than proximal segment 36 and the distal segment 64 when the catheter open distal end 12 becomes lodged against a vessel wall 14 (e.g., where the ophthalmic artery 18 branches away from the internal carotid artery 20) and the surgeon is pushing the catheter 10 distally through a blood vessel. More particularly, the catheter 10 may comprise a relaxed configuration in which the proximal segment 36, distal segment 64 and distensible segment 50 are cylindrical in shape and comprise an inner diameter 48, 76 and 62, respectively, of from about 0.04 inches to about 0.10 inches. Preferably, as shown in FIGS. 5-6, the top drawing in FIG. 7A, and FIG. 8 in the relaxed configuration, the proximal, distal and distensible segments 36, 64 and 50 comprise inner diameters that are substantially equal to each other and outer diameters that are substantially equal to each other (i.e., catheter 10 has a substantially uniform inner diameter 100 and a substantially uniform outer diameter 102 throughout the catheter length 28). However, as shown in FIG. 7, the bottom two drawings in FIG. 7A, FIG. 9, FIG. 10 and FIG. 10A, when a surgeon attempts to push the catheters of the present disclosure distally in a blood vessel when the catheter open distal end 12 is lodged against a vessel wall 14 (i.e., when a linear force in the distal direction is applied to the proximal segment 36 and, in response, a linear force in the proximal direction is applied to the catheter open distal end 12), the catheter 10 is configured to self-adjust/transition from the relaxed configuration to a distended configuration in which i) the cross-sectional height and/or width of the distensible segment 50 is configured to increase, the distensible segment 50 is configured to become non-cylindrical, and/or at least one side of the catheter 10 in the distensible segment 50 is configured to bulge outward, and ii) the cross-sectional width, cross-sectional height and length of the proximal segment 36 and the distal segment 64 are configured to remain constant and the proximal segment 36 and the distal segment 64 are configured to remain cylindrical, in order to dislodge the catheter open distal end 12 from the vessel wall 14. Stated otherwise, when a surgeon pushes a prior art catheter 10' in the distal direction when the catheter open distal end 12' is lodged against the vessel wall 14', a proximal portion of the prior art catheter 10' kinks (as shown in FIG. 4), because the vessel wall 14' exerts a force in the proximal direction against the catheter open distal end 12. In contrast, when a surgeon pushes the catheters 10 of the present disclosure in the distal direction when the catheter open distal end 12 is lodged against the vessel wall 14, the proximal portion of the catheter 10 does not kink but instead the distensible segment 50 of the catheter 10 preferably undergoes a conformational change allowing the catheter open distal end 12 to dislodge from the vessel wall 14, as shown in FIG. 9, FIG. 10 and FIG. 10A.

Once the catheter open distal end 12 is dislodged from the open vessel wall 14, the catheter 10 preferably returns to the relaxed configuration, as shown in FIG. 11. In other words, optionally, as shown in FIG. 11, the catheter 10 is configured to self-adjust/transition from the distended configuration to the relaxed configuration when a linear force in the proximal direction ceases being applied to the catheter open distal end 12 (because the catheter open distal end 12 is dislodged).

Figure 10:
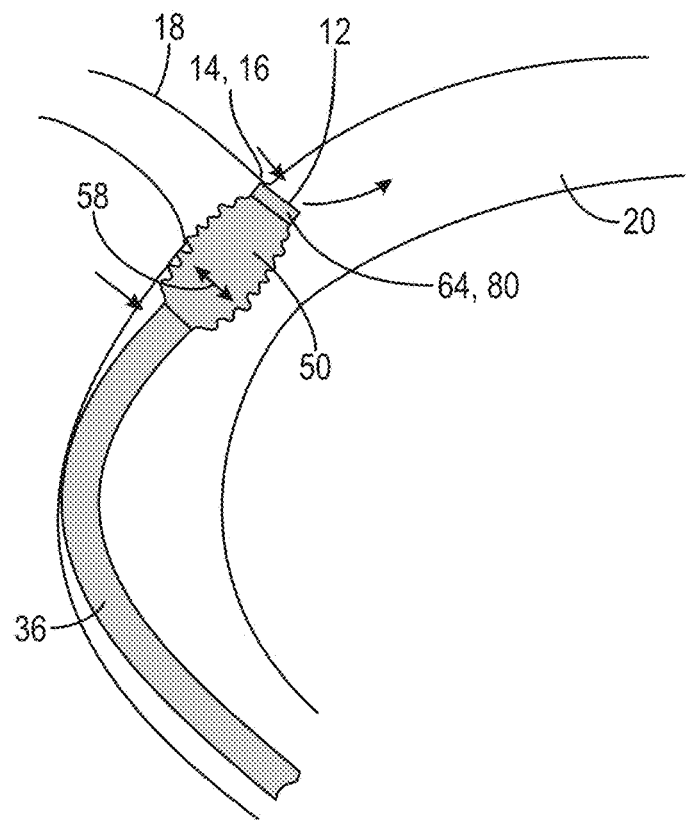
FIG. 10 illustrates how a catheter in accordance with one embodiment of the present invention may self adjust to a distended configuration to dislodge itself from the vessel wall when the surgeon continues to move the catheter proximal end in the distal direction.
Figure 10A:
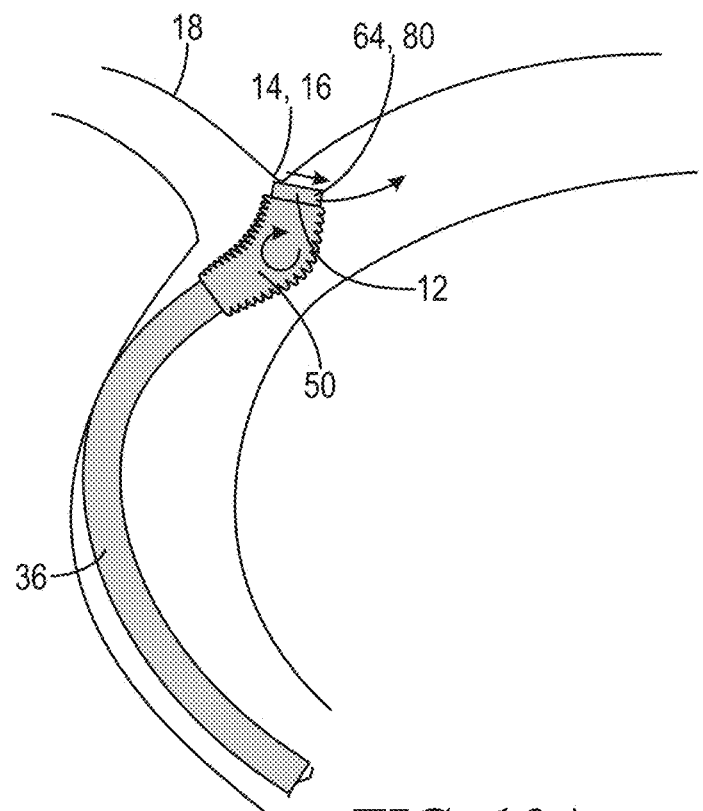
FIG. 10A illustrates how a catheter in accordance with one embodiment of the present invention may self adjust to a distended configuration to dislodge itself from the vessel wall when the surgeon continues to move the catheter proximal end in the distal direction.

For example, in an in vitro flow model designed to mimic the branching of the ophthalmic artery 18 from the internal carotid artery 20, which is shown in FIGS. 1-4, 10 and 10A, catheters 10 designed and assembled as shown in FIGS. 12-28 were seen to self-adjust/transition from the relaxed configuration to the distended configuration shown in FIG. 10 or the distended configuration shown in FIG. 10A, both of which allowed the catheter 10 to dislodge from the vessel wall 14, then return to the relaxed configuration and advance in the internal carotid artery 20 distally beyond the site of the branching of the ophthalmic artery 18, as shown in FIG. 11. By comparison, when the CAT6 Distal Access Catheter (Stryker) was used in the same flow model, it was not able to dislodge from the vessel wall 14 and it was not able to advance in the internal carotid artery 20 distally beyond the site of the branching of the ophthalmic artery 18.

In some embodiments, the proximal segment 36 of the catheter 10 comprises a proximal segment proximal end 38, a proximal segment distal end 40 located proximal to the catheter open distal end 12, a proximal segment length 42 extending from the proximal segment proximal end 38 to the proximal segment distal end 40 and parallel to the catheter length 28, a proximal segment width 44 parallel to the catheter width 32, and a proximal segment height 46 parallel to the catheter height 30. As mentioned previously, the proximal segment 36 is preferably cylindrical in both the relaxed configuration and distended configuration so that the height 46 and width 44 are the merely the outer diameter 88 of the proximal segment 36.

In some embodiments, the distensible segment 50 comprises a proximal end 52 located distal to the proximal segment distal end 40, a distensible segment distal end 54 located proximal to the catheter open distal end 12, a distensible segment length 56 extending from the distensible segment proximal end 52 to the distensible segment distal end 54 and parallel to the catheter length 28, a distensible segment width 58 parallel to the catheter width 32, and a distensible segment height 60 parallel to the catheter height 30. As mentioned previously, the distensible segment 50 is preferably cylindrical in the relaxed configuration so that the height 60 and width 58 in the relaxed configuration are the merely the outer diameter 90 of the distensible segment 50.

In some embodiments, the distal segment 64 comprise a distal segment proximal end 66 located distal to the distensible segment distal end 54, a distal segment distal end 68, a distal segment length 70 extending from the distal segment proximal end 66 to the distal segment distal end 68 and parallel to the catheter length 28, a distal segment width 72 parallel to the catheter width 32, and a distal segment height 74 parallel to the catheter height 30. As mentioned previously, the distal segment 64 is preferably cylindrical in both the relaxed configuration and distended configuration so that the height 74 and width 72 are merely the outer diameter of the distal segment 64.

Optionally, the length of the catheter 10 is from about 100 centimeters to about 165 centimeters.

Figure 7A:
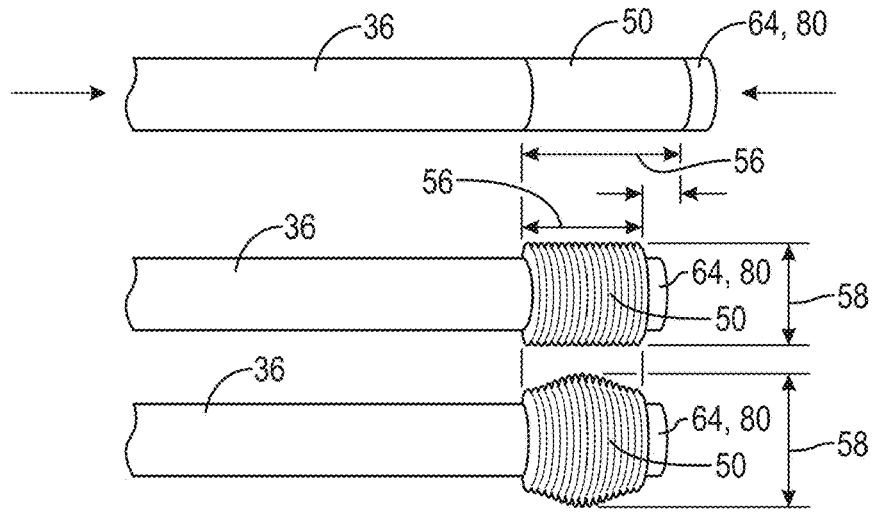
FIG. 7A illustrates a side perspective view of the distal portion of the catheter of another embodiment of the present disclosure, with the top drawing showing the catheter in the relaxed configuration with the arrows showing the proximal and linear forces exerted on the catheter, and the lower two drawings showing how the catheter may respond to that force by widening and shortening in the distensible segment.
Figure 8:
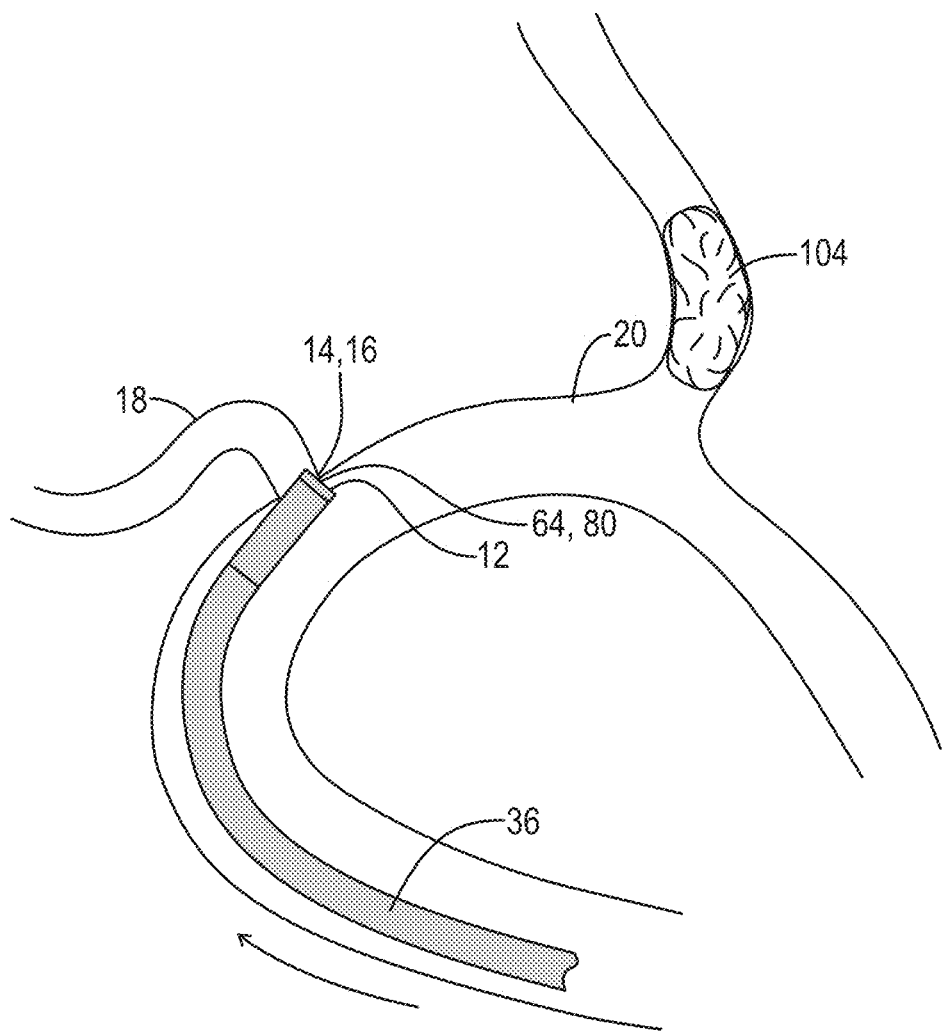
FIG. 8. illustrates a catheter in accordance with one embodiment of the present invention located in a vessel with the distal end of the catheter lodged against the vessel wall.

Optionally, in the distended configuration, the length of the distensible segment 50 is configured to decrease, as shown by comparing FIG. 7 with FIG. 6 and as shown by comparing the bottom drawings in FIG. 7A with the top drawing in FIG. 7A.

Optionally, in the distended configuration, the distensible segment 50 is a non-cylindrical shape (e.g., both sides of the distensible segment 50 may bulge outward as shown in FIGS. 7 and 7A and FIG. 10, one side may bulge outward to a greater degree than an opposite side of the catheter 10 or one side of the distensible segment 50 may shorten and curve inward and an opposite side may lengthen and bulge outward, as shown in FIG. 10A).

Optionally, the length of the distensible segment 50 is from about 5 millimeters to about 10 millimeters. Optionally, the length 42 of the proximal segment 36 is greater than the length 70 of the distal segment 64. For example, optionally, the length 42 of the proximal segment 36 is at least ten times greater than the length 56 of the distensible segment 50 and the length 70 of the distal segment 64. Optionally, the length 56 of the distensible segment 50 is greater than the length 70 of the distal segment 64.

Optionally, the distal end 68 of the distensible segment 50 is located about 0.5 millimeters to about 5 millimeters from the catheter open distal end 12 (e.g., preferably about 1.5 mm from the catheter open distal end 12).

Optionally, the catheter proximal end 22 is coupled to a suction source (not shown). Optionally, the catheter proximal end 22 comprises a hub 78 that may be tapered, shown in FIG. 11B, to allow the catheter proximal end 22 to be coupled to a suction source. Optionally, the suction source is a syringe or pump. Suction sources for aspiration catheters are well known and an example includes the PENUMBRA ENGINE aspiration source, which is said to deliver and maintain nearly pure vacuum (−29.2 inHg or 98.9 kPa).

Optionally, as shown in FIGS. 7A-28, the distal segment 64 comprises a cylindrical metallic band 80 located distal to the distensible segment distal end 54 and adjacent to the catheter distal end 12. Optionally, the cylindrical metallic band 80 is located from about 0 millimeters to about 5 millimeters distal to the distensible segment distal end 54 (e.g., about 1-2 mm). Optionally, the cylindrical metallic band 80 is located at or adjacent the catheter open distal end 12, e.g., from about 0 millimeters to about 5 millimeters proximal to the catheter open distal end 12 (e.g., about 1-2 mm).

Optionally, the cylindrical metallic band 80 comprises a length 82 parallel to the catheter length 28 and optionally the length 82 of the cylindrical metallic band 80 is less than the length 56 of the distensible segment 50. For example, in a non-limiting example, the cylindrical metallic band 80 has a length 82 of from about 0.02 inches to about 0.10 inches (e.g., about 0.03-0.06 inches), an inner diameter 84 of from about 0.04 inches to about 0.10 inches and an outer diameter 86 of from about 0.05 inches to about 0.10 inches. Optionally, the cylindrical metallic band 80 serves as an x-ray marker and is more visible under x-ray as compared to the distensible segment 50 when the catheter 10 is located in a cranial blood vessel inside the body of a human and the x-ray is taken from outside the human's body. Optionally, the cylindrical metallic band 80 is comprised of tantalum, platinum and/or iridium. In the embodiments shown in FIGS. 8-28, in addition to serving as x-ray marker, the cylindrical metallic band 80 makes the distal segment 64 stiff and prevents the distal segment 64 from shortening and widening in the distended configuration. Optionally, the cylindrical metallic band 80, the proximal segment 36 and the distensible segment 50 have substantially the same size inner diameters in the relaxed configuration. Optionally, the cylindrical metallic band 80, the proximal segment 36 and the distensible segment 50 have substantially the same size outer diameters in the relaxed configuration. Optionally, the cylindrical metallic band 80 is rigid. Optionally, because the cylindrical metallic band 80 is rigid, the distal segment 64 is rigid.

Optionally, the distal segment 64 extends from the distensible segment distal end 54 to the catheter open distal end 12.

Optionally, the braid 98, coil 96, outer tube 95, and/or inner tube 94 extend substantially the full length of the catheter 10 (e.g., at least 90% of the full length of the catheter 10). For example, the distal end of the coil 96 may be located under the cylindrical metallic band 80.

Optionally, the proximal segment 36 extends from the catheter proximal end 22 to the distensible segment proximal end 52.

Optionally, the catheter 10 further comprises a wall 92 extending from at least the proximal segment 36 to the distal segment 64 (and preferably from the catheter proximal end 22 to the catheter open distal end 12). Optionally, the wall 92 is comprised of an inner tube 94 surrounding the hollow interior 34 and an outer tube 95 extending around the inner tube 94. A detailed view of the outer tube 95 is shown in FIG. 17 and a detailed view of the inner tube 94 is shown in FIG. 18. Optionally, each of the outer tube 95 and inner tube 94 are comprised of an elastomeric material (e.g., polyurethane). Optionally, as shown in FIG. 17, the outer tube 95 is comprised of a plurality of different segments/cylinders 95a-95j (ten segments/cylinders in the illustrated embodiment of FIG. 17, with the longest segment/cylinder 95a being the proximal segment/cylinders, which has a length of 105 centimeters, and the remaining segments/cylinders 95b-95j having a length of between 3-4 centimeters) that are joined and the flexibility of the segments increases moving distally along the length of the outer tube 95. In FIG. 18, the inner tube 94 is comprised of a proximal segment/cylinder 94a having a length of 123 centimeters and a second segment 94b having a length of 17.5 centimeters with 0.5 centimeters of overlap 206 between the segments 94a and 94b. It will be understood that all dimensions are exemplary.

Optionally, the outer tube 95 is attached to the inner tube 94 in the proximal distal 36 and in the distal segment 64. By contrast, optionally, the outer tube 95 is not attached to the inner tube 94 for at least a portion of the distensible segment 50. A catheter 10 comprising these characteristics is shown in the stepwise manufacturing method shown in FIGS. 17-28. It will be understood the manufacturing process illustrated is exemplary and other methods may be used. Optionally the wall further comprises a coil 96, braid 98, and the aforementioned cylindrical metallic band 80, as described below.

Figure 12:
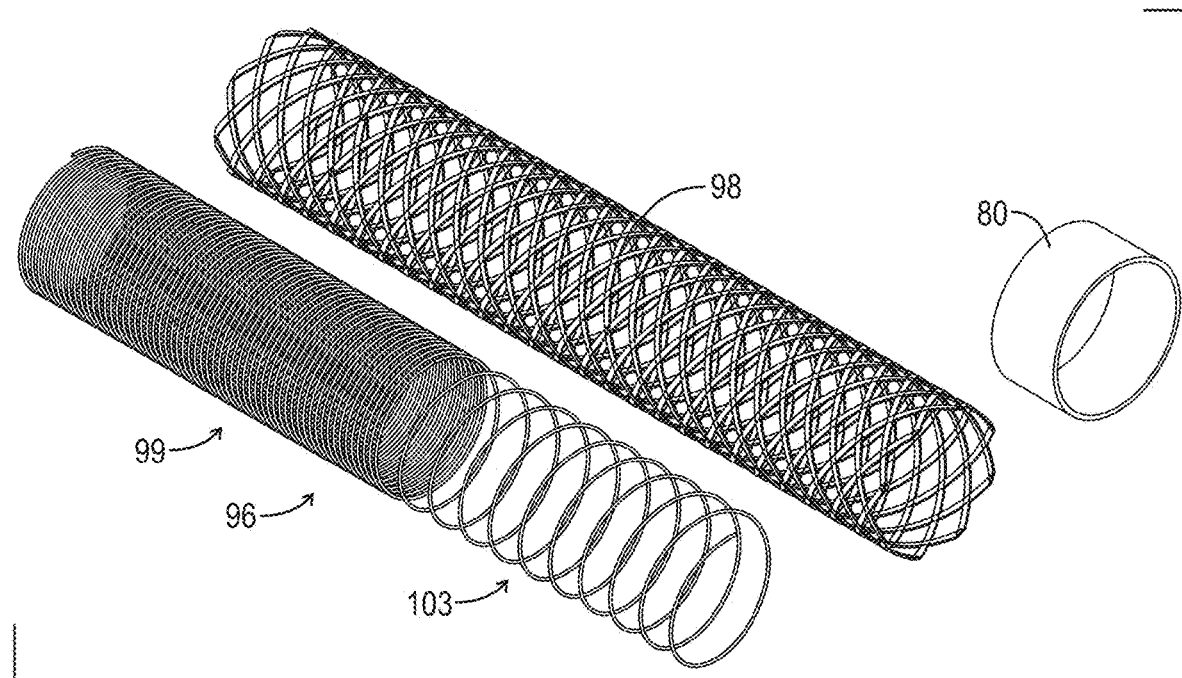
FIG. 12 illustrates a distal portion of the coil, a distal portion of a braid, and a band of a catheter in accordance with one embodiment of the present invention; although not shown, the braid strands are over and under each other.
Figure 13:
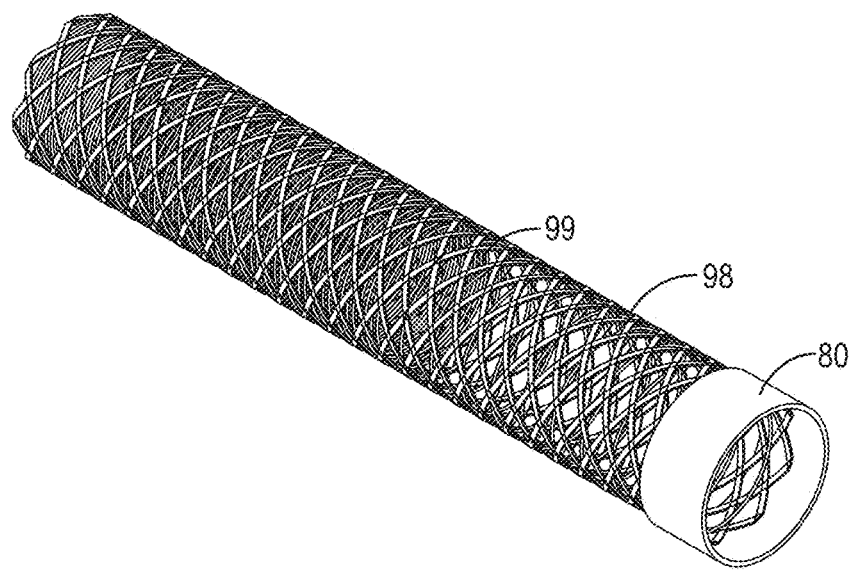
FIG. 13 illustrates how the distal portion of the coil, the distal portion of the braid, and the band of FIG. 12 assemble.
Figure 14:
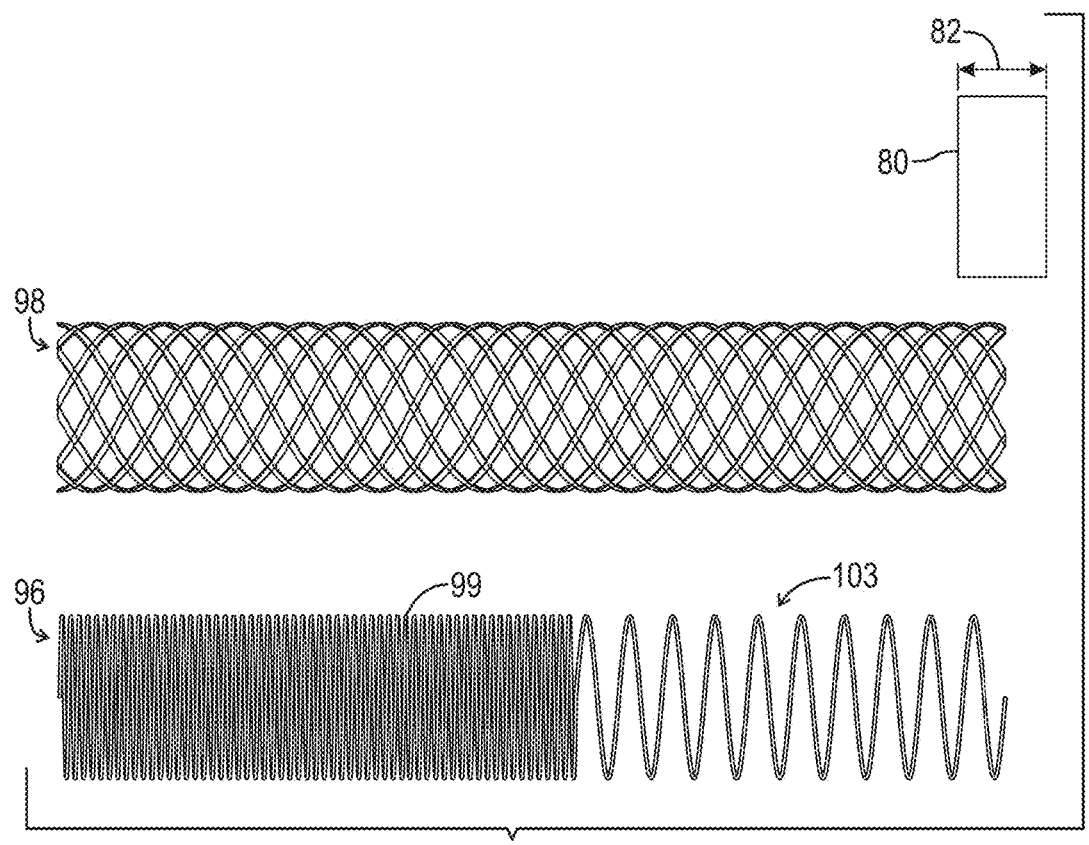
FIG. 14 illustrates a distal portion of the coil, a distal portion of a braid, and a band of a catheter in accordance with one embodiment of the present invention; although not shown, the braid strands are over and under each other.
Figure 15:
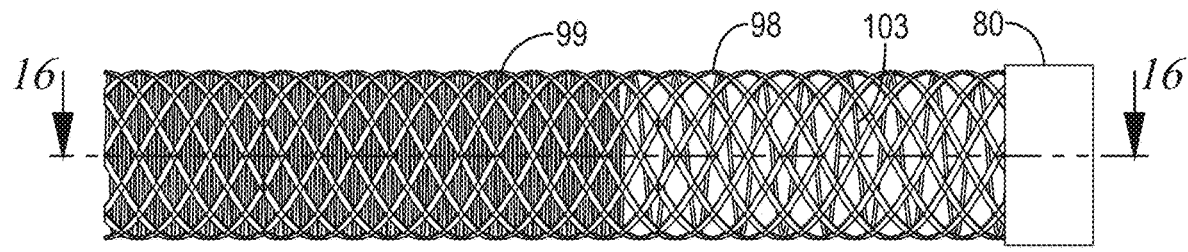
FIG. 15 illustrates how the distal portion of the coil, the distal portion of the braid, and the band of FIG. 14 assemble.
Figure 16:
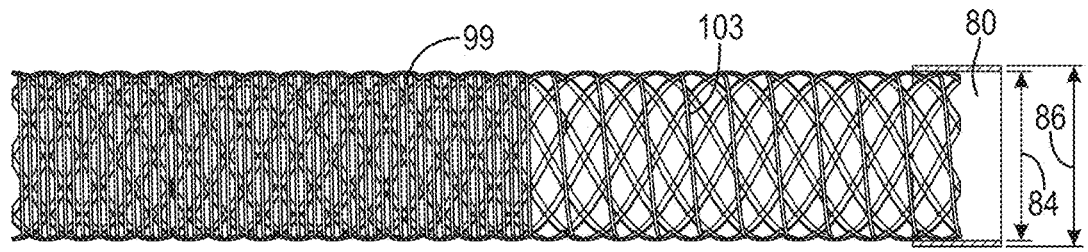
FIG. 16 is a sectional view of the distal portion of the coil, the distal portion of the braid, and the band of FIG. 15 taken along line 16-16 of FIG. 15.

For example, FIGS. 12-13 respectively show an exploded view and an assembled view of a coil 96, metallic band and braid 98 of a catheter 10 of an embodiment of the present invention. In FIG. 12-13, the inner and outer tubes 94 and 95 are not shown for simplicity. The coil 96 extends around the inner tube 94 in a helical manner and as shown in FIGS. 12-16, and 19-28 the pitch of the coil 96 is not uniform throughout the catheter length 28, but rather one segment of the coil 96 has an increased coil pitch (segment labelled as 103) as compared to another segment (segment labelled as 99) of the coil 96. More particularly, the pitch of the coil 96 in the distensible segment 50 is greater than the pitch of the coil 96 in the proximal segment 36. In other words, segment 99 corresponds to the pitch of the coil 96 located in the proximal segment 36 and segment 103 corresponds to the pitch of the coil 96 located in the distensible segment 50. The increased pitch/spacing between adjacent strands of the coil 96 in the distensible segment 50 (together with the fact that, as mentioned above, the outer tube 95 is preferably not attached to the inner tube 94 for at least a portion of the distensible segment 50) allows the distensible segment 50 to self-adjust to the distended configuration while the shape and size of the proximal and distal segments 36 and 64 remains fixed. Optionally, the coil 96 pitch in the distensible segment 50 is between about 0.006 inches to 0.040 inches and optionally the coil 96 pitch in the proximal segment 36 is between about 0.002 to about 0.006 inches. More preferably, the coil 96 pitch in the distensible segment 50 is between about 0.015 inches to 0.040 inches and optionally, the coil 96 pitch in the proximal segment 36 is between about 0.002 inches to about 0.006 inches. For example, in the illustrated embodiment, the pitch of the coil 96 in the proximal segment 36 is 0.004 inches to 0.006 inches and the coil 96 pitch of the distensible segment 50 is 0.20 inches. Accordingly, optionally, the pitch of the coil 96 in the distensible segment 50 is at least three times the pitch of the coil 96 in the proximal segment 36. Optionally, the pitch of the coil 96 in the distal segment 64 (under the metallic band 80) is the same as the pitch of the coil 96 in the distensible segment 50, however, the presence of the metallic band 80 in the distal segment 64 provides rigidity to the distal segment 64 so that its shape and size remain fixed. In addition, optionally, the coil 96 pitch in the proximal segment 36 increases (e.g., from 0.004 to 0.006 inches) as the coil 96 approaches the proximal end 52 of the distensible segment 50.

Figure 20:
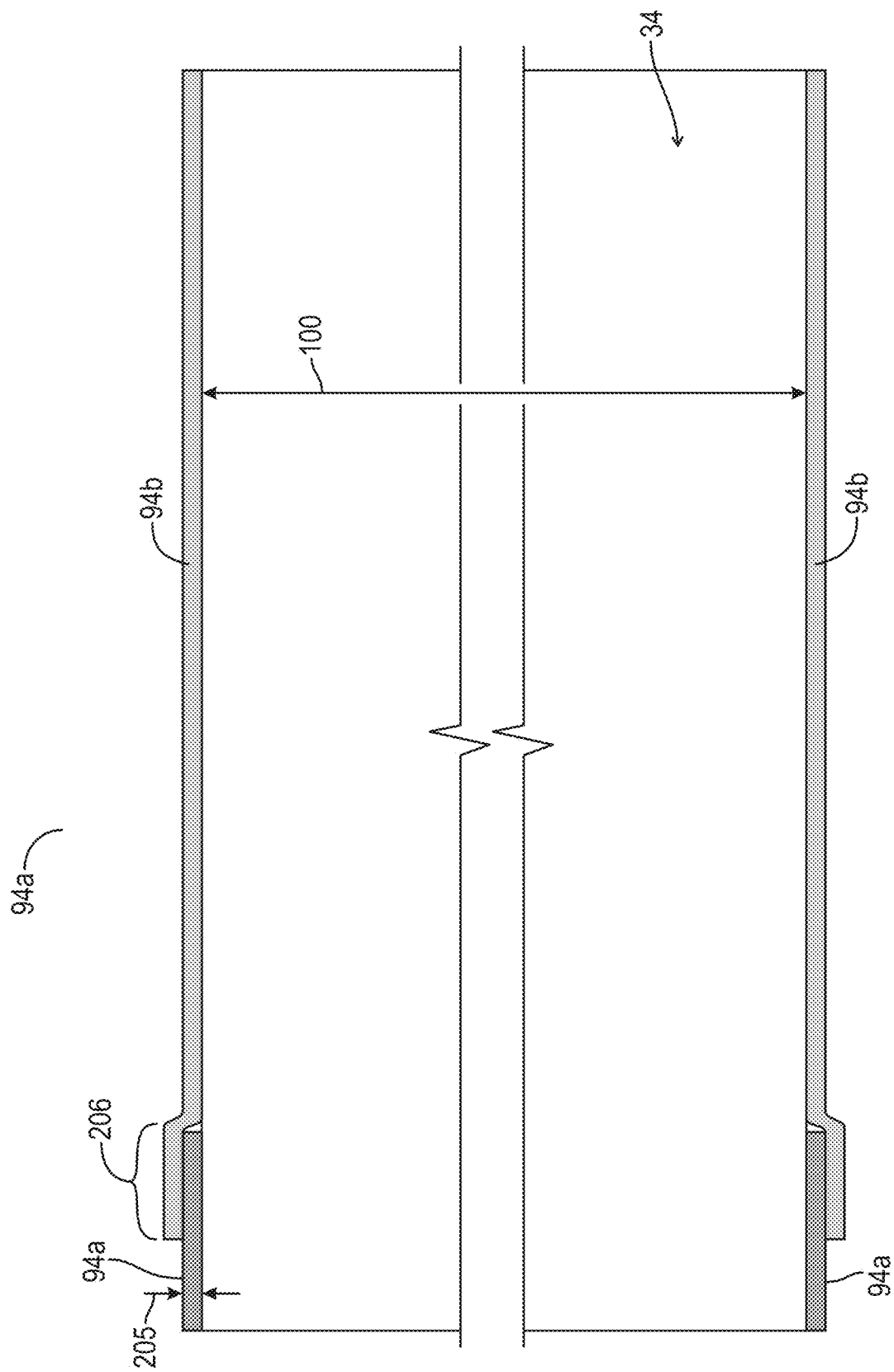
FIGS. 20-21 illustrate a schematic (not to scale) view of an exemplary method of forming of an inner tube of a catheter of an embodiment of the present invention.
Figure 21:
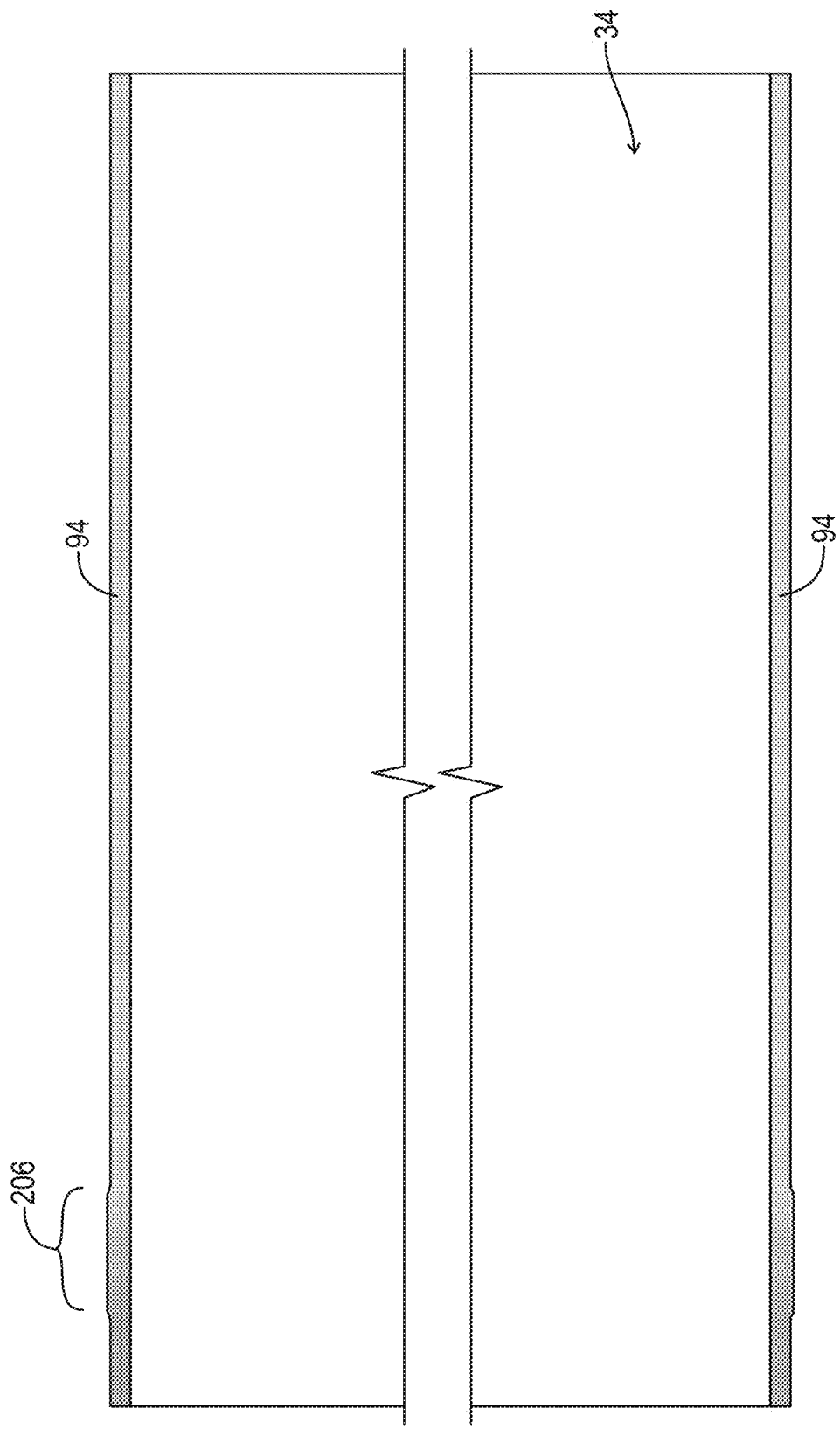
Figure 22:
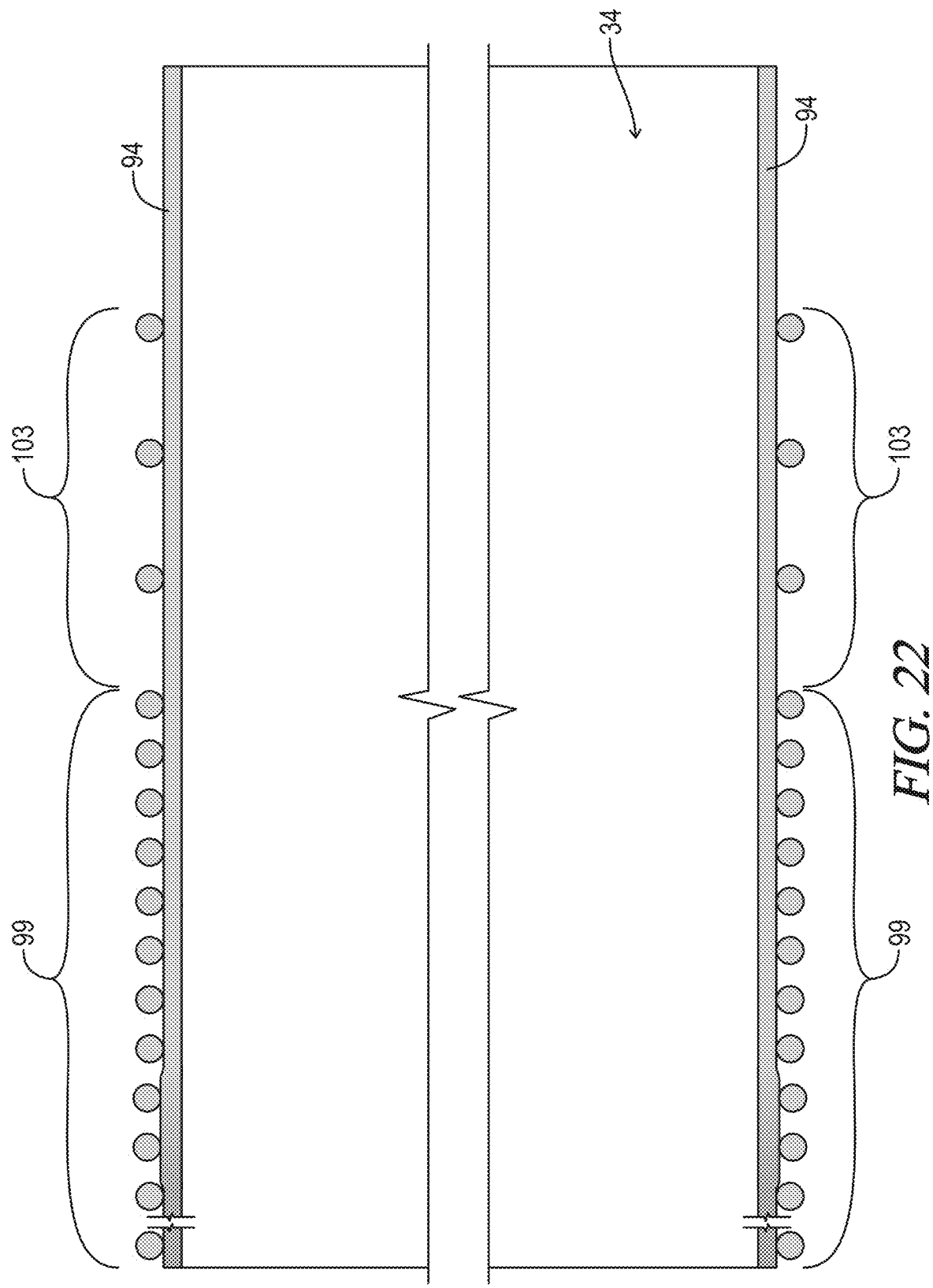
FIGS. 22-23 illustrate a schematic (not to scale) view of an exemplary method of affixing a coil to the inner tube of FIGS. 20-21.
Figure 23:
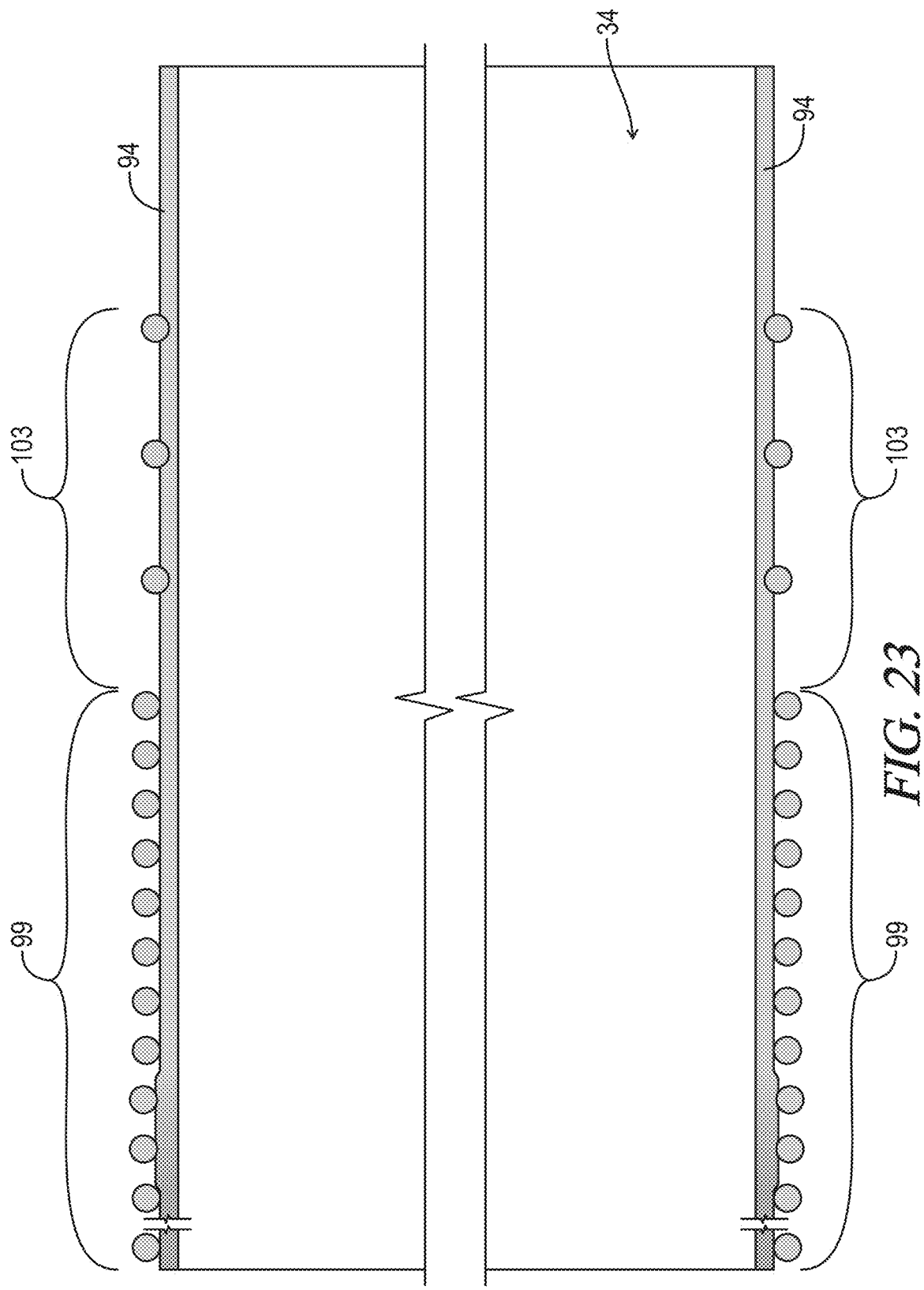
Figure 24:
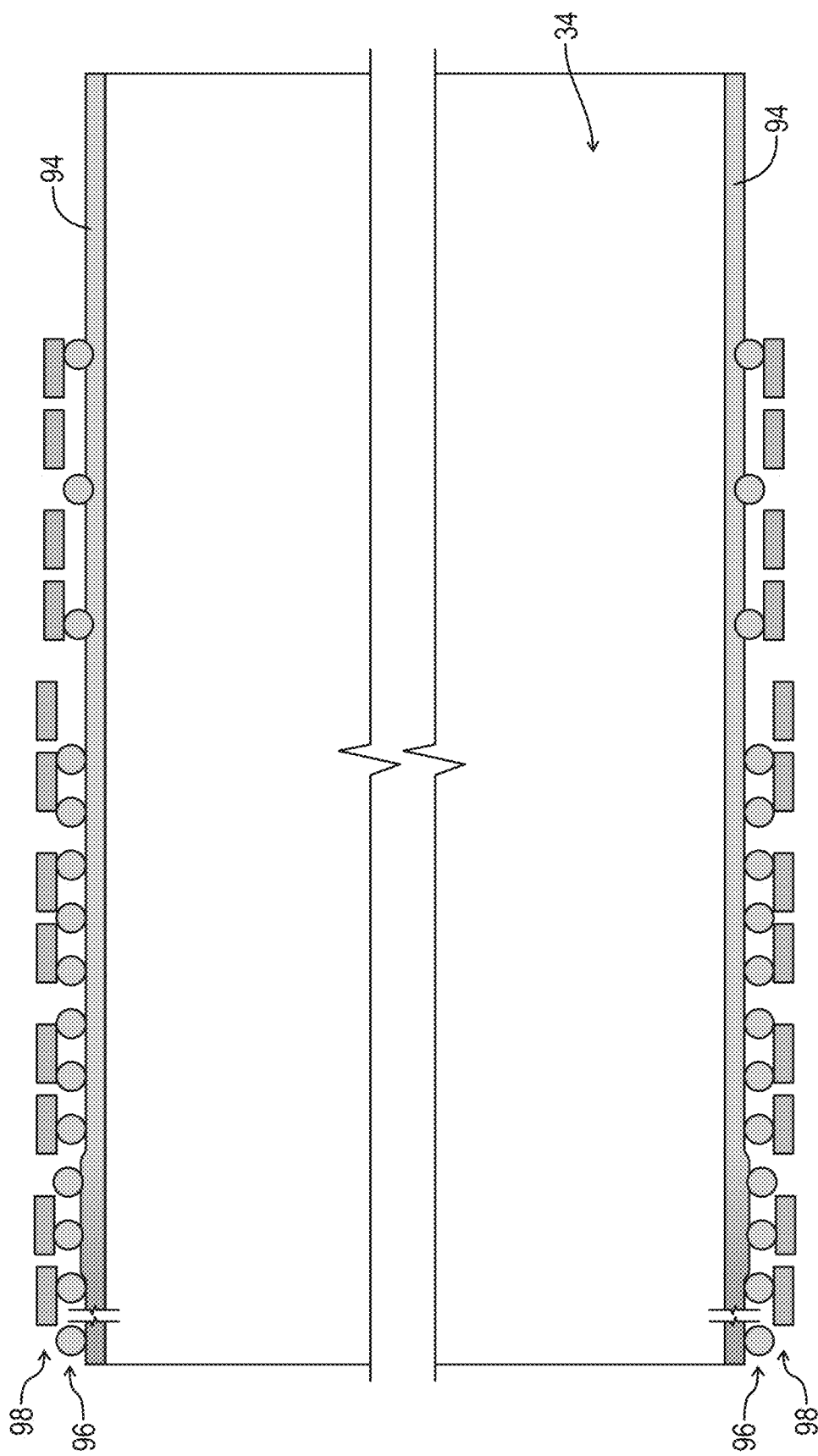
FIGS. 24-25 illustrate a schematic (not to scale) view of an exemplary method of affixing
a braid to the coil of FIGS. 22-23.
Figure 25:
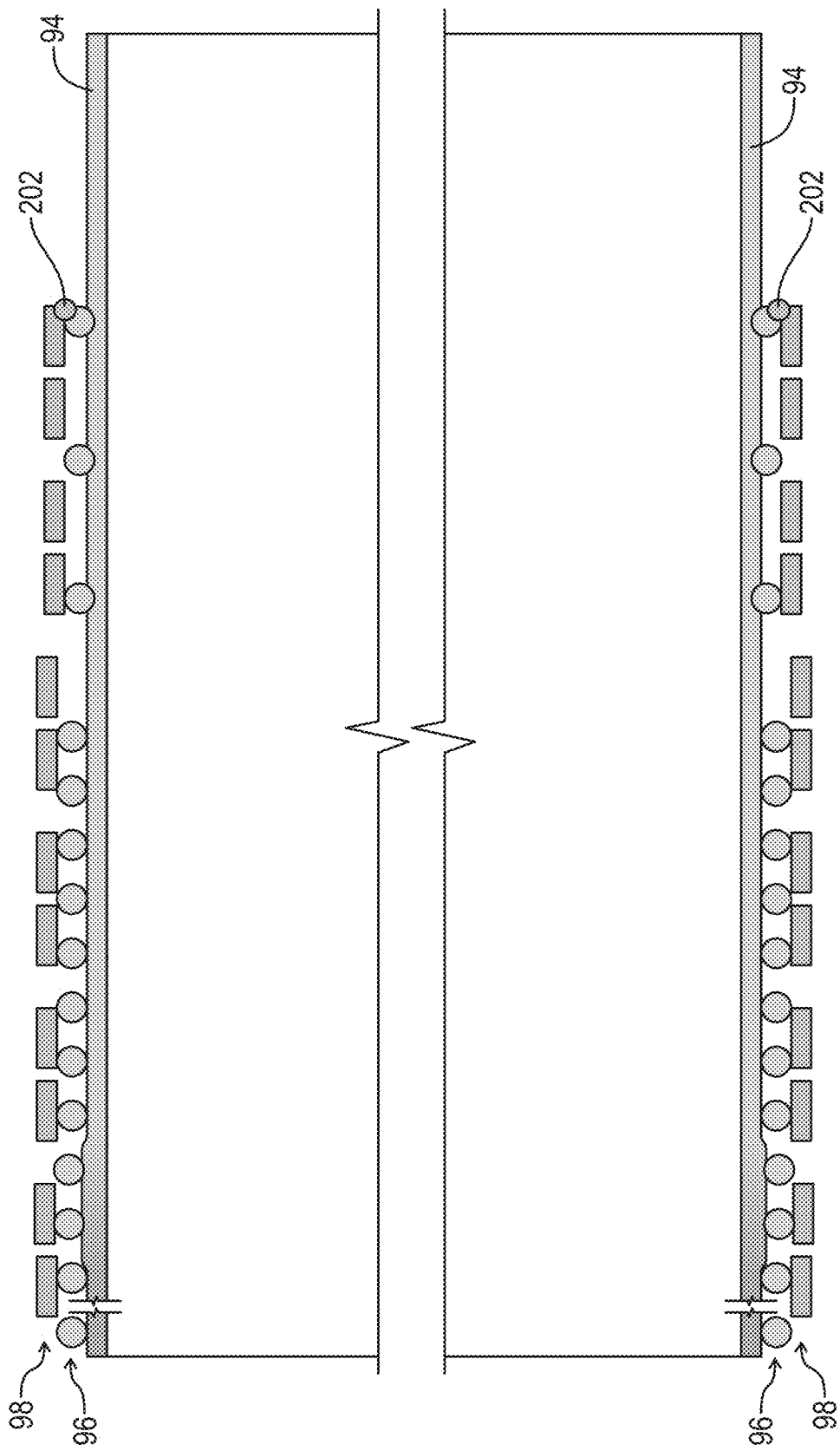
Figure 26:
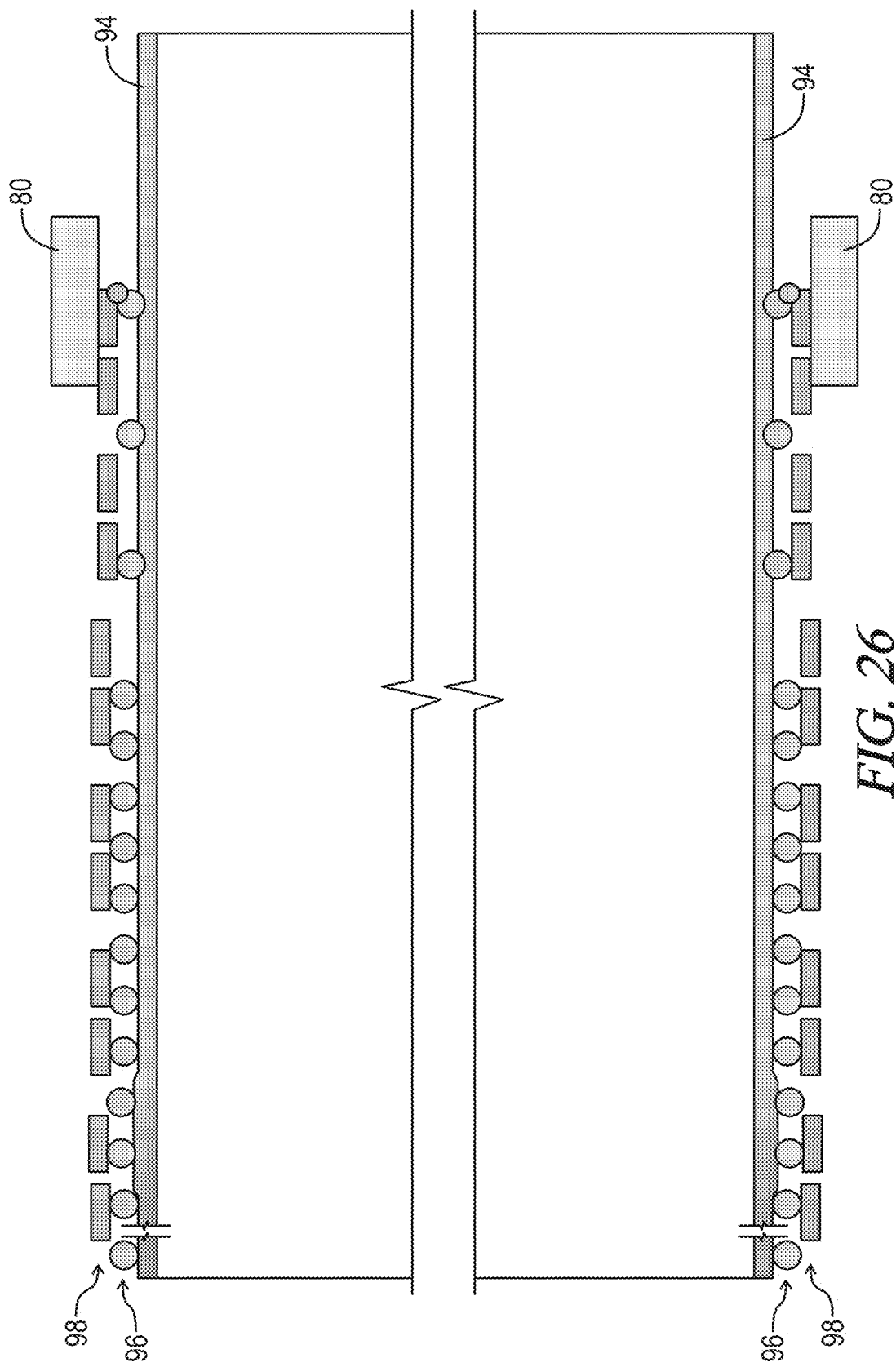
FIG. 26 illustrates a schematic (not to scale) view of an exemplary method of affixing a band to the braid of FIGS. 24-25.
Figure 27:
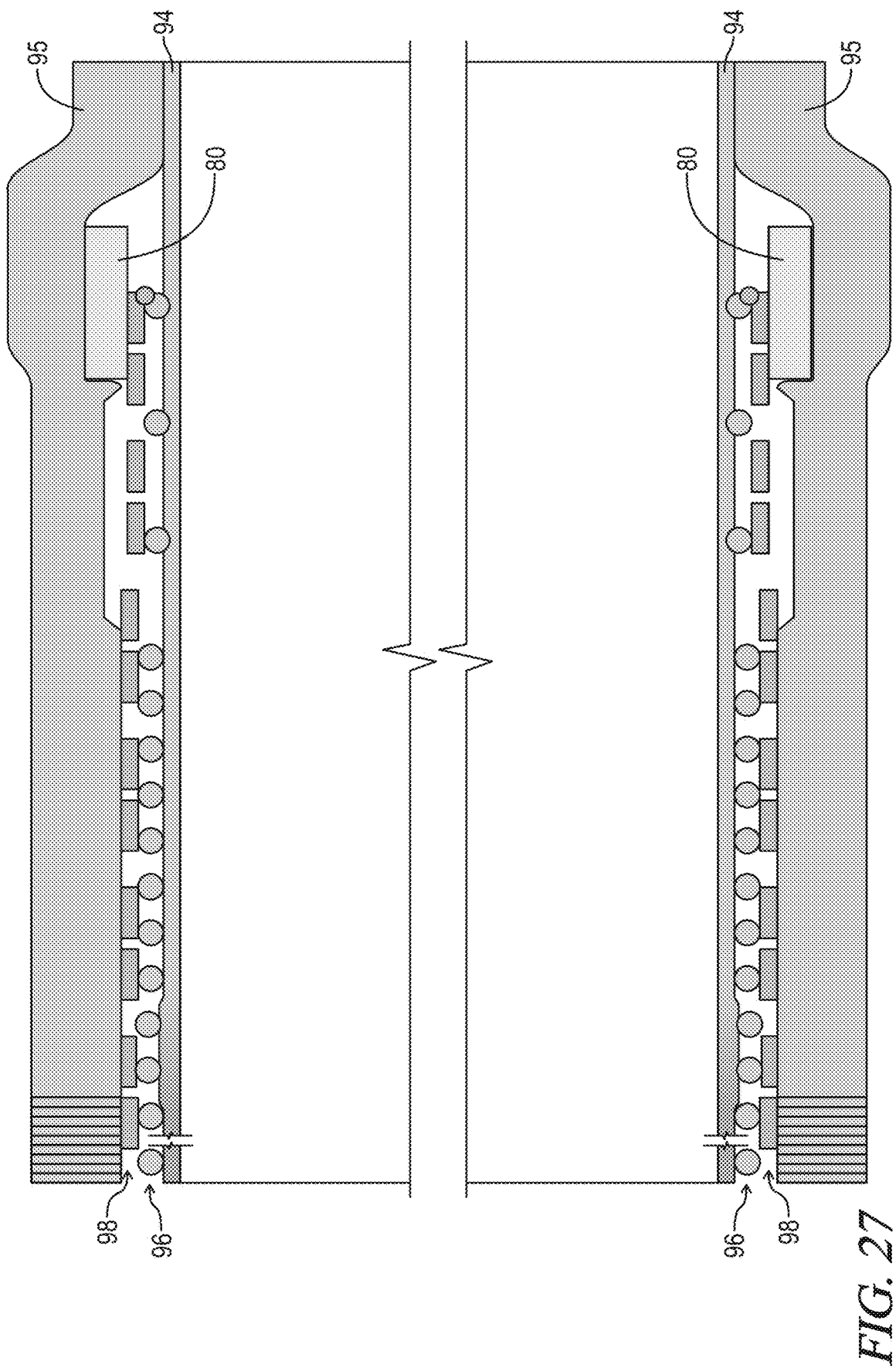
FIGS. 27-28 illustrates a schematic (not to scale) view of an exemplary method of affixing an outer tube to the inner tube, coil and braid of FIGS. 24-25.
Figure 28:
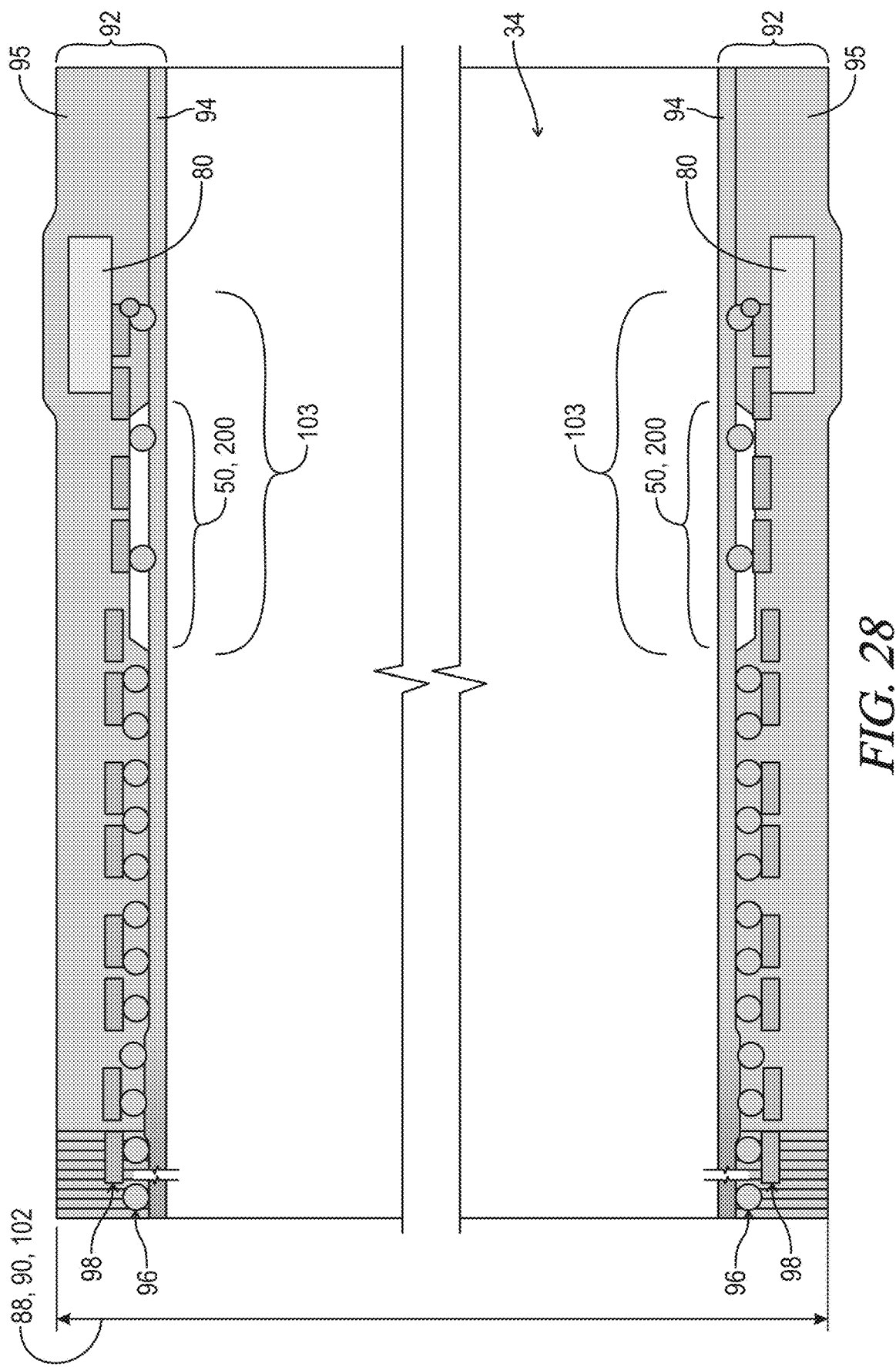

Referring further to the exemplary manufacturing process, FIG. 19 illustrates a detailed view of the coil 96, braid 98 and cylindrical metallic ring 80. It will be understood that all dimensions are exemplary. FIG. 20 illustrates a view of the inner tube 94, which is formed by joining a segment/cylinder comprised of PTFE and with a segment/cylinder comprised of PEBAX 25D with EVERGLIDE. As mentioned above, there is 0.5 centimeter overlap 206 in the segments/cylinders. In FIG. 20, the wall thickness 205 of the inner tube 94 is 0.001 inches. FIG. 21 shows how the PTFE and PEBAX segments fuse together at overlap 206. FIG. 22 illustrates how a coil 96 with a non-uniform pitch is positioned over the inner tube 94 of FIG. 21. In FIG. 22, the coil has a diameter of 0.0015 inches. FIG. 23 illustrates how the distensible segment 50 of the coil 96 (which has the greatest pitch) is fused to the PTFE segment but the proximal segment 36 of the coil 96 is not fused. FIG. 24 illustrates how a braid 98 (e.g., 16 wire, 0.001×0.003 inch rectangular wire) is positioned over the coil 96. FIG. 25 illustrates tack welding of the braid 98 and coil 96 as shown by numeral 202. FIG. 26 illustrates gluing of the metallic band to the braid 98. FIG. 27 illustrates positioning the outer tube 95 over the metallic band, braid 98, coil 96 and inner tube 94. FIG. 28 illustrates fusing the outer tube 95, braid 98, coil 96, and inner tube 94 in the proximal segment 36 and in the distal segment 64 but not in at least a portion 200 of the distensible segment 50. (In FIG. 28, the aforementioned portion 200 is the entire distensible segment 50). This site-specific attachment of the outer tube 95 results in a configuration in which for at least a portion 200 of the distensible segment 50, the coil 96 is attached to the inner tube 94 but not to the outer tube 95, and in which, in the proximal segment 36 and the distal segment 64, the coil 96 is attached to the inner tube 94 and the outer tube 95. Optionally, the catheter 10 is completely built but left on the mandrel (i.e., FIGS. 20-28 take place on a mandrel) and the catheter 10 is coated with a hydrophilic coating to give the catheter 10 lubricity. After coating, tip trimming is performed (cut catheter 10 tip to 1 mm), mandrel removal (remove the build mandrel), hub bonding (cut catheter 10 to length and add hub 78 to proximal end of catheter 10), and packaging. Post packaging is sterilization (EtO—ethylene oxide).

Optionally, as mentioned above, the catheter 10 is coated with a hydrophilic coating.

Optionally, for at least a portion of the distensible segment 50, the braid 98 is attached to the inner tube 94 but not to the outer tube 95, and further wherein, in the proximal segment 36 and the distal segment 64, the braid 98 is attached to the inner tube 94 and the outer tube 95.

Optionally, in the relaxed configuration, the catheter 10 comprises a substantially constant inner diameter 100 and a substantially constant outer diameter 102 along the catheter length 28. For example, in the relaxed configuration, the catheter 10 comprises an inner diameter 100 of from about 0.06 to about 0.08 inches and an outer diameter 102 of from about 0.08 to about 0.1 inches.

Optionally, though not shown, the catheter 10 comprises a plurality of distensible segments (each of which are configured to undergo a conformational change), in which case the catheter may be comprised of a proximal segment located proximal to the distensible segments 50, a distal segment located distal to the distensible segments 50, and one or more intermediary segments, with an intermediary segment between each distensible segment and each intermediary segment having the same characteristics as the proximal and distal segments—i.e., a fixed cylindrical shape, outer diameter and length.

Optionally, the catheter 10 is designed to be used in humans—i.e., comprised of a biocompatible material and is sterile.

Optionally, the catheter 10 is used in a method comprising providing the catheter 10, inserting the catheter open distal end 12 into a human blood vessel and moving the catheter open distal end 12 distally in the human blood vessel. Optionally, the human blood vessel comprises a clot 104, the catheter proximal end 22 is coupled to a suction source, and the method further comprises using suction to draw the clot 104 toward the catheter distal end 12 to remove the clot 104 from the human blood vessel. Optionally, the method further comprises using a stent retriever in conjunction with the catheter 10 to remove the clot 104 from the human blood vessel. Optionally, the method comprises pushing the catheter 10 distally, allowing the catheter open distal end 12 to contact and become stuck against a wall 14 of the human blood vessel (e.g., at ledge of 18 and 20), and continuing to push the catheter 10 distally so that the catheter open distal end 12 moves towards a center of the human blood vessel to become dislodged from the vessel wall 14. Optionally, prior to the catheter open distal end 12 becoming dislodged from the vessel wall 14, i) the height 60 and/or width 58 of the distensible segment 50 increases, the distensible segment 50 becomes non-cylindrical, and/or at least one side of the catheter 10 bulges outward, and ii) the heights 46/74, widths 72/44 and lengths 42 and 70 of the proximal and distal segments 36 and 64 stay constant and the proximal and distal segments 36 and 64 remain cylindrical. Optionally, prior to the catheter open distal end 12 moving towards the center of the human blood vessel to become dislodged from the vessel wall 14, the distensible segment 50 moves away from the vessel wall 14 then towards the vessel wall 14 to cause the catheter open distal end 12 to move towards the center of the human blood vessel to become dislodged from the vessel wall 14. Optionally, the human blood vessel is the internal carotid artery 20. Optionally, the method further comprises moving a microcatheter 106 or other neurovascular device through the hollow interior 34 (e.g., to access a vessel distal to where the ophthalmic artery 18 branches from the internal carotid artery).

Optionally, the aforementioned method does not include placing the catheter 10 through a guide wire—i.e., that the catheter 10 self-adjusts without a guide wire. Optionally, the catheter 10 is used in a method that comprises inserting the catheter distal end 12 into a human, passing the catheter distal end 12 beyond the turns of the cavernous sinus and petrous bone and optionally applying suction to draw a clot 104 or other object into the catheter distal end 12.

Optionally, the catheter 10 is used in conjunction with a stent retriever for retrieving a clot 104. Stent retrievers are described in, for example, U.S. patent application Ser. No. 17/741,673, the entire contents of which are incorporated herein by reference.

| Part List | |
|---|---|
| Catheter | 10 |
| Catheter distal end | 12 |
| Vessel wall | 14 |
| Ledge | 16 |
| Ophthalmic artery | 18 |
| Internal carotid artery | 20 |
| Catheter proximal end | 22 |
| Catheter length | 28 |
| Catheter height | 30 |
| Catheter width | 32 |
| Catheter interior/lumen | 34 |
| Proximal segment | 36 |
| Proximal segment proximal end | 38 |
| Proximal segment distal end | 40 |
| Proximal segment length | 42 |
| Proximal segment width | 44 |
| Proximal segment height | 46 |
| Proximal segment inner diameter | 48 |
| Distensible segment | 50 |
| Distensible segment proximal end | 52 |
| Distensible segment distal end | 54 |
| Distensible segment length | 56 |
| Distensible segment width | 58 |
| Distensible segment height | 60 |
| Distensible segment inner diameter | 62 |
| Distal segment | 64 |
| Distal segment proximal end | 66 |
| Distal segment distal end | 68 |
| Distal segment length | 70 |
| Distal segment width | 72 |
| Distal segment height | 74 |
| Distal segment inner diameter | 76 |
| Proximal hub | 78 |
| Cylindrical metallic band | 80 |
| Cylindrical metallic band length | 82 |
| Cylindrical band inner diameter | 84 |
| Cylindrical band outer diameter | 86 |
| Proximal segment outer diameter | 88 |
| Distensible segment outer diameter | 90 |
| Catheter wall | 92 |
| Inner tube | 94 |
| Outer tube | 95 |
| Coil | 96 |
| Braid | 98 |
| Segment with smaller coil pitch | 99 |
| Catheter inner diameter | 100 |
| Catheter outer diameter | 102 |
| Segment with larger coil pitch | 103 |
| Clot | 104 |
| Distal vessel | 105 |
| Microcatheter | 106 |
| Unbounded area | 200 |
| Tack weld | 202 |
| Overlap between two segments of inner tube | 206 |

Those skilled in the art will understand how to make changes and modifications to the disclosed embodiments to meet their specific requirements or conditions. Changes and modifications may be made without departing from the scope and spirit of the invention. It is understood that use of the singular embraces the plural and vice versa. In addition, the steps of any method described herein may be performed in any suitable order and steps may be performed simultaneously if needed.

Terms of degree such as "generally", "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies. In addition, the steps of the methods described herein can be performed in any suitable order, including simultaneously.

What is claimed is:

1. A catheter comprising:
   a catheter proximal end;
   a catheter open distal end;
   a length extending from the catheter proximal end to the catheter open distal end;
   a height perpendicular to the length;
   a width perpendicular to the length and height;
   a hollow interior extending from the catheter proximal end to the catheter open distal end;
   a proximal segment comprising a proximal segment proximal end, a proximal segment distal end located proximal to the catheter open distal end, a proximal segment length extending from the proximal segment proximal end to the proximal segment distal end and parallel to the catheter length, a proximal segment width parallel to the catheter width, and a proximal segment height parallel to the catheter height;
   a distensible segment comprising a distensible segment proximal end located distal to the proximal segment distal end, a distensible segment distal end located proximal to the catheter open distal end, a distensible segment length extending from the distensible segment proximal end to the distensible segment distal end and parallel to the catheter length, a distensible segment width parallel to the catheter width, and a distensible segment height parallel to the catheter height, the distensible segment comprising a distensible segment interior defining a portion of the hollow interior;
   a distal segment comprising a distal segment proximal end located distal to the distensible segment distal end, a distal segment distal end, a distal segment length extending from the distal segment proximal end to the distal segment distal end and parallel to the catheter length, a distal segment width parallel to the catheter width, and a distal segment height parallel to the catheter height;
   wherein the length of the catheter is from about 100 centimeters to about 165 centimeters;
   wherein the catheter comprises a relaxed configuration in which the proximal, distal and distensible segments are cylindrical in shape and comprise an inner diameter of from about 0.04 inches to about 0.10 inches;
   wherein, when a linear force in the distal direction is applied to the proximal segment while the open distal end is lodged against a vessel wall of the human blood vessel, and in response, a linear force in the proximal direction is applied to the catheter open distal end, the linear forces are configured to cause the catheter to self-adjust from the relaxed configuration to a distended configuration in which i) the height and/or width of the distensible segment is configured to increase, the distensible segment is configured to become non-cylindrical, and/or at least one side of the catheter in the distensible segment is configured to bulge outward, and ii) the width, height and length of the proximal and distal segments are configured to remain constant and the proximal and distal segments are configured to remain cylindrical.

2. The catheter of claim 1 wherein, in the distended configuration, the proximal segment does not kink.

3. The catheter of claim 1 wherein the catheter is configured to self-adjust from the distended configuration to the relaxed configuration when the catheter open distal end dislodges from the vessel wall and the linear force in the proximal direction ceases being applied to the catheter open distal end.

4. The catheter of claim 1 wherein the distal segment comprises a cylindrical metallic band located distal to the distensible segment distal end and adjacent to the catheter open distal end.

5. The catheter of claim 4 wherein the cylindrical metallic band is rigid, is located from about 0 millimeters to about 5 millimeters distal to the distensible segment distal end and is located from about 0 millimeters to about 5 millimeters proximal to the catheter open distal end.

6. The catheter of claim 4 wherein the cylindrical metallic band comprises a length parallel to the catheter length and further wherein the length of the cylindrical metallic band is less than the length of the distensible segment.

7. The catheter of claim 4 wherein the cylindrical metallic band is rigid and is more visible under x-ray as compared to the distensible segment when the catheter is located in a cranial blood vessel inside the body of a human and the x-ray is taken from outside the human's body.

8. The catheter of claim 4 wherein the cylindrical metallic band, the proximal segment, the distensible segment have substantially the same inner diameter in the relaxed configuration and further wherein the cylindrical metallic band, the proximal segment, the distal segment and the distensible segment have substantially the same outer diameter in the relaxed configuration.

9. The catheter of claim 1 wherein the catheter further comprises a wall extending from at least the proximal segment to the distal segment, the wall comprised of an inner tube surrounding the hollow interior and an outer tube extending around the inner tube, wherein the outer tube is attached to the inner tube in the proximal and distal segments, and further wherein the outer tube is not attached to the inner tube for at least a portion of the distensible segment.

10. The catheter of claim 9 wherein the wall of at least a portion of the proximal segment and at least a portion of the distensible segment further comprises a coil located between the outer tube and the inner tube, wherein, for at least a portion of the distensible segment, the coil is attached to the inner tube but not to the outer tube, and further wherein, in the proximal segment, the coil is attached to the inner tube and the outer tube.

11. The catheter of claim 10 wherein the coil extends around the inner tube in a helical manner, the coil comprising a variable coil pitch, and further wherein the coil pitch in the distensible segment is greater than the coil pitch in the proximal segment.

12. The catheter of claim 11 wherein the wall further comprises a braid located between the coil and the outer tube.

13. The catheter of claim 12 wherein the distal segment comprises a rigid cylindrical metallic band located distal to the distensible segment distal end and adjacent to the catheter open distal end, the rigid cylindrical metallic band attached to the braid.

14. The catheter of claim 12 wherein, for at least a portion of the distensible segment, the braid is attached to the inner tube but not to the outer tube, and further wherein, in the proximal segment, the braid is attached to the inner tube and the outer tube.

15. The catheter of claim 10 wherein the coil pitch in the distensible segment is between about 0.006 to 0.040 inches and further wherein the coil pitch in the proximal segment is between about 0.002 to about 0.006 inches.

16. The catheter of claim 10 wherein the coil pitch in the distensible segment is at least three times greater in the distensible segment than the proximal segment.

17. The catheter of claim 10 wherein the inner tube and the outer tube are comprised of an elastomeric material.

18. The catheter of claim 10 wherein the distal end of the distensible segment is located about 0.5 millimeters to about 5 millimeters from the catheter open distal end.

19. The catheter of claim 1 wherein the distal segment extends from the distensible segment distal end to the catheter open distal end.

20. The catheter of claim 1 wherein the proximal segment extends from the catheter proximal end to the distensible segment proximal end.

21. The catheter of claim 1 wherein the length of the distensible segment is from about 5 millimeters to about 10 millimeters and further wherein the length of the proximal segment is at least ten times greater than the length of the distensible segment and the length of the distal segment.

22. The catheter of claim 1 wherein, in the distended configuration, a first side of the distensible segment is configured to shorten and curve inward and an opposite side of the distensible segment is configured to lengthen and bulge outward.

23. The catheter of claim 1 wherein the distal end of the distensible segment is located about 0.5 millimeters to about 5 millimeters from the catheter open distal end.

24. The catheter of claim 1 wherein the catheter is coupled to a suction source located adjacent to the catheter proximal end.

25. The catheter of claim 1 wherein, in the relaxed configuration, the catheter comprises a substantially constant inner diameter and a substantially constant outer diameter along the catheter length, wherein the catheter is coated with a hydrophilic coating and further wherein the catheter is comprised of a biocompatible material and is sterile.

26. A method of using the catheter in a human vascular system comprising providing the catheter of claim 1, inserting the catheter open distal end into the human vascular system and moving the catheter open distal end distally in the human blood vessel.

27. The method of claim 26, wherein a human blood vessel of the human vascular system comprises a clot, the catheter proximal end is coupled to a suction source, and the method further comprises using suction to draw the clot toward the catheter open distal end to remove the clot from the human blood vessel.

28. A method of using the catheter in a human vascular system comprising providing the catheter of claim 1, inserting the catheter open distal end into the human vascular system and passing the catheter open distal end beyond the turns of the cavernous sinus and petrous bone without the catheter open distal end being covered by another catheter.

29. A catheter comprising:
a catheter proximal end;
a catheter open distal end;
a length extending from the catheter proximal end to the catheter open distal end;
a height perpendicular to the length;
a width perpendicular to the length and height;
a hollow interior extending from the catheter proximal end to the catheter open distal end;

a proximal segment comprising a proximal segment proximal end, a proximal segment distal end located proximal to the catheter open distal end, a proximal segment length extending from the proximal segment proximal end to the proximal segment distal end and parallel to the catheter length, a proximal segment width parallel to the catheter width, and a proximal segment height parallel to the catheter height;

a distensible segment comprising a distensible segment proximal end located distal to the proximal segment distal end, a distensible segment distal end located proximal to the catheter open distal end, a distensible segment length extending from the distensible segment proximal end to the distensible segment distal end and parallel to the catheter length, a distensible segment width parallel to the catheter width, and a distensible segment height parallel to the catheter height;

a distal segment comprising a distal segment proximal end located distal to the distensible segment distal end, a distal segment distal end, a distal segment length extending from the distal segment proximal end to the distal segment distal end and parallel to the catheter length, a distal segment width parallel to the catheter width, and a distal segment height parallel to the catheter height;

wherein the length of the catheter is from about 100 centimeters to about 165 centimeters;

wherein the catheter comprises a relaxed configuration in which the proximal, distal and distensible segments are cylindrical in shape and comprise an inner diameter of from about 0.04 inches to about 0.10 inches;

wherein the catheter further comprises a wall extending from at least the proximal segment to the distal segment, the wall comprised of an inner tube defining the hollow interior and an outer tube extending around the inner tube, wherein the outer tube is attached to the inner tube in the proximal and distal segments, and further wherein the outer tube is not attached to the inner tube for at least a portion of the distensible segment, wherein the wall of at least a portion of the proximal segment and at least a portion of the distensible segment further comprises a coil located between the outer tube and the inner tube, wherein, for at least a portion of the distensible segment, the coil is attached to the inner tube but not to the outer tube, wherein, in the proximal segment, the coil is attached to the inner tube and the outer tube; and further wherein the coil extends around the inner tube in a helical manner, the coil comprising a variable coil pitch, and further wherein the coil pitch in the distensible segment is greater than the coil pitch in the proximal segment.

30. The catheter of claim 29, wherein the wall further comprises a braid located between the coil and the outer tube;

wherein the distal segment comprises a rigid cylindrical metallic band located distal to the distensible segment distal end and adjacent to the catheter open distal end, the rigid cylindrical metallic band attached to the braid;

wherein, for at least a portion of the distensible segment, the braid is attached to the inner tube but not to the outer tube, and further wherein, in the proximal segment, the braid is attached to the inner tube and the outer tube;

wherein the coil pitch in the distensible segment is between about 0.006 to 0.040 inches and further wherein the coil pitch in the proximal segment is between about 0.002 to about 0.006 inches, and wherein the coil pitch in the distensible segment is at least three times greater in the distensible segment than the proximal segment.

* * * * *